US008840642B2

(12) United States Patent
Euteneuer et al.

(10) Patent No.: US 8,840,642 B2
(45) Date of Patent: *Sep. 23, 2014

(54) METHODS AND APPARATUS FOR FIXING SHEET-LIKE MATERIALS TO A TARGET TISSUE

(71) Applicant: Rotation Medical, Inc., Plymouth, MN (US)

(72) Inventors: Charles L. Euteneuer, St. Michael, MN (US); Rebecca McCarville, Spring Park, MN (US); Duane Frion, Brooklyn Center, MN (US); Nathaniel Zenz-Olson, Blaine, MN (US); Diane M. Feehan, Corcoran, MN (US)

(73) Assignee: Rotation Medical, Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/172,601

(22) Filed: Feb. 4, 2014

(65) Prior Publication Data
US 2014/0188161 A1    Jul. 3, 2014

Related U.S. Application Data

(63) Continuation of application No. 12/794,540, filed on Jun. 4, 2010, now Pat. No. 8,668,718.

(60) Provisional application No. 61/313,051, filed on Mar. 11, 2010, provisional application No. 61/253,800, filed on Oct. 21, 2009, provisional application No. 61/184,198, filed on Jun. 4, 2009.

(51) Int. Cl.
A61B 17/08        (2006.01)
A61B 17/064       (2006.01)

(52) U.S. Cl.
CPC ................................ *A61B 17/0642* (2013.01)
USPC ............................................................. 606/219

(58) Field of Classification Search
USPC ................... 606/75, 213, 215, 219, 220, 224; 227/19, 175.1, 908; 41/457
See application file for complete search history.

(56) References Cited

U.S. PATENT DOCUMENTS 511,238 A    12/1893  Hieatzman et al.
765,793 A    7/1904   Ruckel
(Continued)

FOREIGN PATENT DOCUMENTS

CA    2390508 A1    5/2001
EP    0142225 A1    5/1985
(Continued)

OTHER PUBLICATIONS

Alexander et al., "Ligament and tendon repair with an absorbable polymer-coated carbon fiber stent," Bulletin of the Hospital for Joint Diseases Orthopaedic Institute; vol. 46; No. 2; pp. 155-173; 1986.

(Continued)

*Primary Examiner* — Jonathan W Miles
(74) *Attorney, Agent, or Firm* — Seager, Tufte & Wickhem LLC

(57) ABSTRACT

A staple for attaching a sheet-like implant to tissue or bone may include first and second arms, and first and second flukes. In some embodiments, the first arm has a proximal end and a distal end, and the second arm has a proximal end and a distal end. A bridge extends from the proximal end of the first arm to the proximal end of the second arm. The first fluke has a proximal end abutting the distal end of the first arm, and the first fluke extends distally from the first arm. The first fluke has a lateral extent larger than a lateral extent of the first arm and is mounted eccentrically thereto. The first fluke includes a proximal surface projecting at an outward angle in a proximal direction away from the distal end of the first arm to engage the tissue or bone when inserted therein. The second fluke has similar features. This arrangement causes the first and second flukes to rotate in response to a pullout force on the bridge. Methods for attaching a sheet-like implant to a target tissue are also disclosed.

20 Claims, 16 Drawing Sheets

(56) References Cited

U.S. PATENT DOCUMENTS

| | | |
|---|---|---|
| 1,728,316 A | 9/1929 | Von Wachenfeldt et al. |
| 1,855,546 A | 4/1932 | File |
| 1,868,100 A | 7/1932 | Goodstein |
| 1,910,688 A | 5/1933 | Goodstein |
| 1,940,351 A | 12/1933 | Howard |
| 2,034,785 A | 3/1936 | Wappler |
| 2,075,508 A | 3/1937 | Davidson |
| 2,131,321 A | 9/1938 | Hart |
| 2,158,242 A | 5/1939 | Maynard |
| 2,199,025 A | 4/1940 | Conn |
| 2,201,610 A | 5/1940 | Dawson, Jr. |
| 2,254,620 A | 9/1941 | Miller |
| 2,277,931 A | 3/1942 | Moe |
| 2,283,814 A | 5/1942 | La Place |
| 2,316,297 A | 4/1943 | Southerland et al. |
| 2,421,193 A | 5/1947 | Gardner |
| 2,571,813 A | 10/1951 | Austin |
| 2,630,316 A | 3/1953 | Foster |
| 2,684,070 A | 7/1954 | Kelsey |
| 2,744,251 A | 5/1956 | Vollmer |
| 2,790,341 A | 4/1957 | Keep et al. |
| 2,817,339 A | 12/1957 | Sullivan |
| 2,825,162 A | 3/1958 | Flood |
| 2,881,762 A | 4/1959 | Lowrie |
| 2,910,067 A | 10/1959 | White |
| 3,068,870 A | 12/1962 | Levin |
| 3,077,812 A | 2/1963 | Dietrich |
| 3,103,666 A | 9/1963 | Bone |
| 3,123,077 A | 3/1964 | Alcamo |
| 3,209,754 A | 10/1965 | Brown |
| 3,221,746 A | 12/1965 | Noble |
| 3,470,834 A | 10/1969 | Bone |
| 3,527,223 A | 9/1970 | Shein |
| 3,570,497 A | 3/1971 | Lemole |
| 3,577,837 A | 5/1971 | Bader, Jr. |
| 3,579,831 A | 5/1971 | Stevens et al. |
| 3,643,851 A | 2/1972 | Green et al. |
| 3,687,138 A | 8/1972 | Jarvik |
| 3,716,058 A | 2/1973 | Tanner, Jr. |
| 3,717,294 A | 2/1973 | Green |
| 3,757,629 A | 9/1973 | Schneider |
| 3,777,538 A | 12/1973 | Weatherly et al. |
| 3,837,555 A | 9/1974 | Green |
| 3,845,772 A | 11/1974 | Smith |
| 3,875,648 A | 4/1975 | Bone |
| 3,960,147 A | 6/1976 | Murray |
| 3,976,079 A | 8/1976 | Samuels et al. |
| 4,014,492 A | 3/1977 | Rothfuss |
| 4,127,227 A | 11/1978 | Green |
| 4,259,959 A | 4/1981 | Walker |
| 4,263,903 A | 4/1981 | Griggs |
| 4,265,226 A | 5/1981 | Cassimally |
| 4,317,451 A | 3/1982 | Cerwin et al. |
| 4,400,833 A | 8/1983 | Kurland |
| 4,422,567 A | 12/1983 | Haynes |
| 4,454,875 A | 6/1984 | Pratt et al. |
| 4,480,641 A | 11/1984 | Failla et al. |
| 4,485,816 A | 12/1984 | Krumme |
| 4,526,174 A | 7/1985 | Froehlich |
| 4,549,545 A | 10/1985 | Levy |
| 4,570,623 A | 2/1986 | Ellison et al. |
| 4,595,007 A | 6/1986 | Mericle |
| 4,624,254 A | 11/1986 | McGarry et al. |
| 4,627,437 A | 12/1986 | Bedi et al. |
| 4,632,100 A | 12/1986 | Somers et al. |
| 4,635,637 A | 1/1987 | Schreiber |
| 4,669,473 A | 6/1987 | Richards et al. |
| 4,696,300 A | 9/1987 | Anderson |
| 4,719,917 A | 1/1988 | Barrows et al. |
| 4,738,255 A | 4/1988 | Goble et al. |
| 4,741,330 A | 5/1988 | Hayhurst |
| 4,762,260 A | 8/1988 | Richards et al. |
| 4,799,495 A | 1/1989 | Hawkins et al. |
| 4,809,695 A | 3/1989 | Gwathmey et al. |
| 4,851,005 A | 7/1989 | Hunt et al. |
| 4,858,608 A | 8/1989 | McQuilkin |
| 4,884,572 A | 12/1989 | Bays et al. |
| 4,887,601 A | 12/1989 | Richards |
| 4,924,866 A | 5/1990 | Yoon |
| 4,930,674 A | 6/1990 | Barak |
| 4,968,315 A | 11/1990 | Gatturna |
| 4,976,715 A | 12/1990 | Bays et al. |
| 4,994,073 A | 2/1991 | Green |
| 4,997,436 A | 3/1991 | Oberlander |
| 5,002,563 A | 3/1991 | Pyka et al. |
| 5,013,316 A | 5/1991 | Goble et al. |
| 5,015,249 A | 5/1991 | Nakao et al. |
| 5,037,422 A | 8/1991 | Hayhurst et al. |
| 5,041,129 A | 8/1991 | Hayhurst et al. |
| 5,046,513 A | 9/1991 | Gatturna et al. |
| 5,053,047 A | 10/1991 | Yoon |
| 5,059,206 A | 10/1991 | Winters |
| 5,062,563 A | 11/1991 | Green et al. |
| 5,100,417 A | 3/1992 | Cerier et al. |
| 5,102,421 A | 4/1992 | Anspach, Jr. |
| 5,116,357 A | 5/1992 | Eberbach |
| 5,122,155 A | 6/1992 | Eberbach |
| 5,123,913 A | 6/1992 | Wilk et al. |
| RE34,021 E | 8/1992 | Mueller et al. |
| 5,141,515 A | 8/1992 | Eberbach |
| 5,141,520 A | 8/1992 | Goble et al. |
| 5,156,609 A | 10/1992 | Nakao et al. |
| 5,156,616 A | 10/1992 | Meadows et al. |
| 5,167,665 A | 12/1992 | McKinney |
| 5,171,259 A | 12/1992 | Inoue |
| 5,174,295 A | 12/1992 | Christian et al. |
| 5,174,487 A | 12/1992 | Rothfuss et al. |
| 5,176,682 A | 1/1993 | Chow |
| 5,176,692 A | 1/1993 | Wilk et al. |
| 5,203,787 A | 4/1993 | Noblitt et al. |
| 5,217,472 A | 6/1993 | Green et al. |
| 5,224,946 A | 7/1993 | Hayhurst et al. |
| 5,242,457 A | 9/1993 | Akopov et al. |
| 5,246,441 A | 9/1993 | Ross et al. |
| 5,251,642 A | 10/1993 | Handlos |
| 5,261,914 A | 11/1993 | Warren |
| 5,269,753 A | 12/1993 | Wilk |
| 5,269,783 A | 12/1993 | Sander |
| 5,282,829 A | 2/1994 | Hermes |
| 5,289,963 A | 3/1994 | McGarry et al. |
| 5,290,217 A | 3/1994 | Campos |
| 5,304,187 A | 4/1994 | Green et al. |
| 5,333,624 A | 8/1994 | Tovey |
| 5,342,396 A | 8/1994 | Cook |
| 5,350,400 A | 9/1994 | Esposito et al. |
| 5,352,229 A | 10/1994 | Goble et al. |
| 5,354,292 A | 10/1994 | Braeuer et al. |
| 5,364,408 A | 11/1994 | Gordon |
| 5,366,460 A | 11/1994 | Eberbach |
| 5,370,650 A | 12/1994 | Tovey et al. |
| 5,372,604 A | 12/1994 | Trott |
| 5,380,334 A | 1/1995 | Torrie et al. |
| 5,383,477 A | 1/1995 | DeMatteis |
| 5,397,332 A | 3/1995 | Kammerer et al. |
| 5,403,326 A | 4/1995 | Harrison et al. |
| 5,405,360 A | 4/1995 | Tovey |
| 5,411,522 A | 5/1995 | Trott |
| 5,411,523 A | 5/1995 | Goble |
| 5,417,691 A | 5/1995 | Hayhurst |
| 5,417,712 A | 5/1995 | Whittaker et al. |
| 5,425,490 A | 6/1995 | Goble et al. |
| 5,441,502 A | 8/1995 | Bartlett |
| 5,441,508 A | 8/1995 | Gazielly et al. |
| 5,456,720 A | 10/1995 | Schultz et al. |
| 5,464,403 A | 11/1995 | Kieturakis et al. |
| 5,478,354 A | 12/1995 | Tovey et al. |
| 5,486,197 A | 1/1996 | Le et al. |
| 5,497,933 A | 3/1996 | DeFonzo et al. |
| 5,500,000 A | 3/1996 | Feagin et al. |
| 5,501,695 A | 3/1996 | Anspach, Jr. et al. |
| 5,503,623 A | 4/1996 | Tilton, Jr. |
| 5,505,735 A | 4/1996 | Li |
| 5,507,754 A | 4/1996 | Green et al. |
| 5,520,700 A | 5/1996 | Beyar et al. |

(56) References Cited

U.S. PATENT DOCUMENTS

| | | | |
|---|---|---|---|
| 5,522,817 A | 6/1996 | Sander et al. |
| 5,545,180 A | 8/1996 | Le et al. |
| 5,560,532 A | 10/1996 | DeFonzo et al. |
| 5,562,689 A | 10/1996 | Green et al. |
| 5,569,306 A | 10/1996 | Thal |
| 5,582,616 A | 12/1996 | Bolduc et al. |
| 5,584,835 A | 12/1996 | Greenfield |
| 5,618,314 A | 4/1997 | Harwin et al. |
| 5,622,257 A | 4/1997 | Deschenes et al. |
| 5,628,751 A | 5/1997 | Sander et al. |
| 5,643,319 A | 7/1997 | Green et al. |
| 5,643,321 A | 7/1997 | McDevitt |
| 5,647,874 A | 7/1997 | Hayhurst |
| 5,649,963 A | 7/1997 | McDevitt |
| 5,662,683 A | 9/1997 | Kay |
| 5,667,513 A | 9/1997 | Torrie et al. |
| 5,674,245 A | 10/1997 | Ilgen |
| 5,681,342 A | 10/1997 | Benchetrit |
| 5,702,215 A | 12/1997 | Li |
| 5,713,903 A | 2/1998 | Sander et al. |
| 5,720,753 A | 2/1998 | Sander et al. |
| 5,725,541 A | 3/1998 | Anspach, III et al. |
| 5,741,282 A | 4/1998 | Anspach, III et al. |
| 5,766,246 A | 6/1998 | Mulhauser et al. |
| 5,782,864 A | 7/1998 | Lizardi |
| 5,797,909 A | 8/1998 | Michelson |
| 5,797,931 A | 8/1998 | Bito et al. |
| 5,797,963 A | 8/1998 | McDevitt |
| 5,807,403 A | 9/1998 | Beyar et al. |
| 5,830,221 A | 11/1998 | Stein et al. |
| 5,836,961 A | 11/1998 | Kieturakis et al. |
| 5,868,762 A | 2/1999 | Cragg et al. |
| 5,873,891 A | 2/1999 | Sohn |
| 5,885,294 A | 3/1999 | Pedlick et al. |
| 5,893,856 A | 4/1999 | Jacob et al. |
| 5,904,696 A | 5/1999 | Rosenman |
| 5,919,184 A | 7/1999 | Tilton, Jr. |
| 5,922,026 A | 7/1999 | Chin |
| 5,928,244 A | 7/1999 | Tovey et al. |
| 5,948,000 A | 9/1999 | Larsen et al. |
| 5,957,939 A | 9/1999 | Heaven et al. |
| 5,957,953 A | 9/1999 | DiPoto et al. |
| 5,968,044 A | 10/1999 | Nicholson et al. |
| 5,980,557 A | 11/1999 | Iserin et al. |
| 5,989,265 A | 11/1999 | Bouquet De La Joliniere et al. |
| 5,997,552 A | 12/1999 | Person et al. |
| 6,063,088 A | 5/2000 | Winslow |
| 6,156,045 A | 12/2000 | Ulbrich et al. |
| 6,179,840 B1 | 1/2001 | Bowman |
| 6,193,731 B1 | 2/2001 | Oppelt et al. |
| 6,193,733 B1 | 2/2001 | Adams |
| 6,245,072 B1 | 6/2001 | Zdeblick et al. |
| 6,302,885 B1 | 10/2001 | Essiger |
| 6,312,442 B1 | 11/2001 | Kieturakis et al. |
| 6,315,789 B1 | 11/2001 | Cragg |
| 6,318,616 B1 | 11/2001 | Pasqualucci et al. |
| 6,322,563 B1 | 11/2001 | Cummings et al. |
| 6,325,805 B1 | 12/2001 | Ogilvie et al. |
| 6,387,113 B1 | 5/2002 | Hawkins et al. |
| 6,391,333 B1 | 5/2002 | Li et al. |
| 6,413,274 B1 | 7/2002 | Pedros |
| 6,425,900 B1 | 7/2002 | Knodel et al. |
| 6,436,110 B2 | 8/2002 | Bowman et al. |
| 6,447,522 B2 | 9/2002 | Gambale et al. |
| 6,447,524 B1 | 9/2002 | Knodel et al. |
| 6,478,803 B1 | 11/2002 | Kapec et al. |
| 6,482,178 B1 | 11/2002 | Andrews et al. |
| 6,482,210 B1 | 11/2002 | Skiba et al. |
| 6,506,190 B1 | 1/2003 | Walshe |
| 6,511,499 B2 | 1/2003 | Schmieding et al. |
| 6,517,564 B1 | 2/2003 | Grafton et al. |
| 6,524,316 B1 | 2/2003 | Nicholson et al. |
| 6,527,795 B1 | 3/2003 | Lizardi |
| 6,530,933 B1 | 3/2003 | Yeung et al. |
| 6,540,769 B1 | 4/2003 | Miller, III |
| 6,551,333 B2 | 4/2003 | Kuhns et al. |
| 6,554,852 B1 | 4/2003 | Oberlander |
| 6,569,186 B1 | 5/2003 | Winters et al. |
| 6,575,976 B2 | 6/2003 | Grafton |
| 6,599,289 B1 | 7/2003 | Bojarski et al. |
| 6,620,185 B1 | 9/2003 | Harvie et al. |
| 6,629,988 B2 | 10/2003 | Weadock |
| 6,638,297 B1 | 10/2003 | Huitema |
| 6,648,893 B2 | 11/2003 | Dudasik |
| 6,666,872 B2 | 12/2003 | Barreiro et al. |
| 6,673,094 B1 | 1/2004 | McDevitt et al. |
| 6,685,728 B2 | 2/2004 | Sinnott et al. |
| 6,692,506 B1 | 2/2004 | Ory et al. |
| 6,723,099 B1 | 4/2004 | Goshert |
| 6,726,704 B1 | 4/2004 | Loshakove et al. |
| 6,726,705 B2 | 4/2004 | Peterson et al. |
| 6,740,100 B2 | 5/2004 | Demopulos et al. |
| 6,746,472 B2 | 6/2004 | Frazier et al. |
| 6,764,500 B1 | 7/2004 | Van De Moer et al. |
| 6,770,073 B2 | 8/2004 | McDevitt et al. |
| 6,779,701 B2 | 8/2004 | Bailly et al. |
| 6,800,081 B2 | 10/2004 | Parodi |
| 6,835,206 B2 | 12/2004 | Jackson |
| 6,849,078 B2 | 2/2005 | Durgin et al. |
| 6,887,259 B2 | 5/2005 | Lizardi |
| 6,926,723 B1 | 8/2005 | Mulhauser et al. |
| 6,932,834 B2 | 8/2005 | Lizardi et al. |
| 6,939,365 B1 | 9/2005 | Fogarty et al. |
| 6,946,003 B1 | 9/2005 | Wolowacz et al. |
| 6,949,117 B2 | 9/2005 | Gambale et al. |
| 6,964,685 B2 | 11/2005 | Murray et al. |
| 6,966,916 B2 | 11/2005 | Kumar |
| 6,972,027 B2 | 12/2005 | Fallin et al. |
| 6,984,241 B2 | 1/2006 | Lubbers et al. |
| 6,991,597 B2 | 1/2006 | Gellman et al. |
| 7,008,435 B2 | 3/2006 | Cummins |
| 7,021,316 B2 | 4/2006 | Leiboff |
| 7,025,772 B2 | 4/2006 | Gellman et al. |
| 7,033,379 B2 | 4/2006 | Peterson |
| 7,037,324 B2 | 5/2006 | Martinek |
| 7,048,171 B2 | 5/2006 | Thornton et al. |
| 7,063,711 B1 | 6/2006 | Loshakove et al. |
| 7,083,638 B2 | 8/2006 | Foerster |
| 7,087,064 B1 | 8/2006 | Hyde |
| 7,112,214 B2 | 9/2006 | Peterson et al. |
| 7,118,581 B2 | 10/2006 | Fridén |
| 7,144,413 B2 | 12/2006 | Wilford et al. |
| 7,144,414 B2 | 12/2006 | Harvie et al. |
| 7,150,750 B2 | 12/2006 | Dmaarati |
| 7,153,314 B2 | 12/2006 | Laufer et al. |
| 7,160,314 B2 | 1/2007 | Sgro et al. |
| 7,160,326 B2 | 1/2007 | Ball |
| 7,163,551 B2 | 1/2007 | Anthony et al. |
| 7,163,563 B2 | 1/2007 | Schwartz et al. |
| 7,169,157 B2 | 1/2007 | Kayan |
| 7,189,251 B2 | 3/2007 | Kay |
| 7,201,754 B2 | 4/2007 | Stewart et al. |
| 7,214,232 B2 | 5/2007 | Bowman et al. |
| 7,226,469 B2 | 6/2007 | Benavitz et al. |
| 7,229,452 B2 | 6/2007 | Kayan |
| 7,247,164 B1 | 7/2007 | Ritchart et al. |
| 7,303,577 B1 | 12/2007 | Dean |
| 7,309,337 B2 | 12/2007 | Coleran et al. |
| 7,320,692 B1 | 1/2008 | Bender et al. |
| 7,320,701 B2 | 1/2008 | Haut et al. |
| 7,322,935 B2 | 1/2008 | Palmer et al. |
| 7,326,231 B2 | 2/2008 | Phillips et al. |
| 7,343,920 B2 | 3/2008 | Toby et al. |
| 7,368,124 B2 | 5/2008 | Chun et al. |
| 7,377,934 B2 | 5/2008 | Lin et al. |
| 7,381,213 B2 | 6/2008 | Lizardi |
| 7,390,329 B2 | 6/2008 | Westra et al. |
| 7,399,304 B2 | 7/2008 | Gambale et al. |
| 7,404,824 B1 | 7/2008 | Webler et al. |
| 7,416,554 B2 | 8/2008 | Lam et al. |
| 7,452,368 B2 | 11/2008 | Liberatore et al. |
| 7,460,913 B2 | 12/2008 | Kuzma et al. |
| 7,463,933 B2 | 12/2008 | Wahlstrom et al. |
| 7,465,308 B2 | 12/2008 | Sikora et al. |

(56) References Cited

U.S. PATENT DOCUMENTS

| | | |
|---|---|---|
| 7,481,832 B1 | 1/2009 | Meridew et al. |
| 7,485,124 B2 | 2/2009 | Kuhns et al. |
| 7,497,854 B2 | 3/2009 | Gill et al. |
| 7,500,972 B2 | 3/2009 | Voegele et al. |
| 7,500,980 B2 | 3/2009 | Gill et al. |
| 7,500,983 B1 | 3/2009 | Kaiser et al. |
| 7,503,474 B2 | 3/2009 | Hillstead et al. |
| 7,506,791 B2 | 3/2009 | Omaits et al. |
| 7,559,941 B2 | 7/2009 | Zannis et al. |
| 7,572,276 B2 | 8/2009 | Lim et al. |
| 7,585,311 B2 | 9/2009 | Green et al. |
| 7,766,208 B2 | 8/2010 | Epperly et al. |
| 7,771,440 B2 | 8/2010 | Ortiz et al. |
| 7,776,057 B2 | 8/2010 | Laufer et al. |
| 7,780,685 B2 | 8/2010 | Hunt et al. |
| 7,785,255 B2 | 8/2010 | Malkani |
| 7,807,192 B2 | 10/2010 | Li et al. |
| 7,819,880 B2 | 10/2010 | Zannis et al. |
| 7,918,879 B2 | 4/2011 | Yeung et al. |
| 8,114,101 B2 | 2/2012 | Criscuolo et al. |
| 8,197,837 B2 | 6/2012 | Jamiolkowski et al. |
| 2002/0077687 A1 | 6/2002 | Ahn |
| 2002/0123767 A1 | 9/2002 | Prestel |
| 2002/0165559 A1 | 11/2002 | Grant et al. |
| 2002/0169465 A1 | 11/2002 | Bowman et al. |
| 2003/0073979 A1 | 4/2003 | Naimark et al. |
| 2003/0125748 A1 | 7/2003 | Li et al. |
| 2003/0212456 A1 | 11/2003 | Lipchitz et al. |
| 2004/0059416 A1 | 3/2004 | Murray et al. |
| 2004/0092937 A1 | 5/2004 | Criscuolo et al. |
| 2004/0138705 A1 | 7/2004 | Heino et al. |
| 2004/0167519 A1 | 8/2004 | Weiner et al. |
| 2005/0015021 A1 | 1/2005 | Shiber |
| 2005/0049618 A1 | 3/2005 | Masuda et al. |
| 2005/0051597 A1 | 3/2005 | Toledano |
| 2005/0059996 A1 | 3/2005 | Bauman et al. |
| 2005/0060033 A1 | 3/2005 | Vacanti et al. |
| 2005/0107807 A1 | 5/2005 | Nakao |
| 2005/0113736 A1 | 5/2005 | Orr et al. |
| 2005/0171569 A1 | 8/2005 | Girard et al. |
| 2005/0187576 A1 | 8/2005 | Whitman et al. |
| 2005/0240222 A1 | 10/2005 | Shipp |
| 2005/0274768 A1 | 12/2005 | Cummins et al. |
| 2006/0074423 A1 | 4/2006 | Alleyne et al. |
| 2006/0178743 A1 | 8/2006 | Carter |
| 2006/0235442 A1 | 10/2006 | Huitema |
| 2006/0293760 A1 | 12/2006 | DeDeyne |
| 2007/0078477 A1 | 4/2007 | Heneveld, Sr. et al. |
| 2007/0083236 A1 | 4/2007 | Sikora et al. |
| 2007/0112361 A1 | 5/2007 | Schonholz et al. |
| 2007/0179531 A1 | 8/2007 | Thornes |
| 2007/0185506 A1 | 8/2007 | Jackson |
| 2007/0190108 A1 | 8/2007 | Datta et al. |
| 2007/0219558 A1 | 9/2007 | Deutsch |
| 2007/0270804 A1 | 11/2007 | Chudik |
| 2007/0288023 A1 | 12/2007 | Pellegrino et al. |
| 2008/0027470 A1 | 1/2008 | Hart et al. |
| 2008/0051888 A1 | 2/2008 | Ratcliffe et al. |
| 2008/0065153 A1 | 3/2008 | Allard et al. |
| 2008/0090936 A1 | 4/2008 | Fujimura et al. |
| 2008/0125869 A1 | 5/2008 | Paz et al. |
| 2008/0135600 A1 | 6/2008 | Hiranuma et al. |
| 2008/0173691 A1 | 7/2008 | Mas et al. |
| 2008/0188874 A1 | 8/2008 | Henderson |
| 2008/0188936 A1 | 8/2008 | Ball et al. |
| 2008/0195119 A1 | 8/2008 | Ferree |
| 2008/0200949 A1 | 8/2008 | Hiles et al. |
| 2008/0241213 A1 | 10/2008 | Chun et al. |
| 2008/0272173 A1 | 11/2008 | Coleman et al. |
| 2008/0306408 A1 | 12/2008 | Lo |
| 2009/0001122 A1 | 1/2009 | Prommersberger et al. |
| 2009/0012521 A1 | 1/2009 | Axelson, Jr. et al. |
| 2009/0030434 A1 | 1/2009 | Paz et al. |
| 2009/0069806 A1 | 3/2009 | De La Mora Levy et al. |
| 2009/0076541 A1 | 3/2009 | Chin et al. |
| 2009/0105535 A1 | 4/2009 | Green et al. |
| 2009/0112085 A1 | 4/2009 | Eby |
| 2009/0134198 A1 | 5/2009 | Knodel et al. |
| 2009/0156986 A1 | 6/2009 | Trenhaile |
| 2009/0156997 A1 | 6/2009 | Trenhaile |
| 2009/0182245 A1 | 7/2009 | Zambelli |
| 2009/0242609 A1 | 10/2009 | Kanner |
| 2010/0145367 A1 | 6/2010 | Ratcliffe |
| 2010/0147922 A1 | 6/2010 | Olson |
| 2010/0163598 A1 | 7/2010 | Belzer |
| 2010/0191332 A1 | 7/2010 | Euteneuer et al. |
| 2010/0241227 A1 | 9/2010 | Euteneuer et al. |
| 2010/0249801 A1 | 9/2010 | Sengun et al. |
| 2010/0256675 A1 | 10/2010 | Romans |
| 2010/0274278 A1 | 10/2010 | Fleenor et al. |
| 2010/0292715 A1 | 11/2010 | Nering et al. |
| 2010/0292791 A1 | 11/2010 | Lu et al. |
| 2010/0312250 A1 | 12/2010 | Euteneuer et al. |
| 2010/0312275 A1 | 12/2010 | Euteneuer et al. |
| 2010/0327042 A1 | 12/2010 | Amid et al. |
| 2011/0000950 A1 | 1/2011 | Euteneuer et al. |
| 2011/0004221 A1 | 1/2011 | Euteneuer et al. |
| 2011/0011917 A1 | 1/2011 | Loulmet |
| 2011/0034942 A1 | 2/2011 | Levin et al. |
| 2011/0040310 A1 | 2/2011 | Levin et al. |
| 2011/0040311 A1 | 2/2011 | Levin et al. |
| 2011/0066166 A1 | 3/2011 | Levin et al. |
| 2011/0106154 A1 | 5/2011 | DiMatteo et al. |
| 2011/0114700 A1 | 5/2011 | Baxter, Iii et al. |
| 2011/0224702 A1 | 9/2011 | Van Kampen et al. |
| 2011/0264149 A1 | 10/2011 | Pappalardo et al. |
| 2012/0160893 A1 | 6/2012 | Harris et al. |
| 2012/0193391 A1 | 8/2012 | Michler et al. |
| 2012/0209401 A1 | 8/2012 | Euteneuer |
| 2012/0211543 A1 | 8/2012 | Euteneuer |
| 2012/0248171 A1 | 10/2012 | Bailly et al. |
| 2013/0153627 A1 | 6/2013 | Euteneuer et al. |
| 2013/0153628 A1 | 6/2013 | Euteneuer |
| 2013/0158554 A1 | 6/2013 | Euteneuer et al. |
| 2013/0158587 A1 | 6/2013 | Euteneuer et al. |
| 2013/0158661 A1 | 6/2013 | Euteneuer et al. |
| 2013/0172920 A1 | 7/2013 | Euteneuer et al. |
| 2013/0172997 A1 | 7/2013 | Euteneuer et al. |
| 2013/0184716 A1 | 7/2013 | Euteneuer et al. |
| 2013/0240598 A1 | 9/2013 | Euteneuer et al. |
| 2013/0245627 A1 | 9/2013 | Euteneuer et al. |
| 2013/0245682 A1 | 9/2013 | Euteneuer et al. |
| 2013/0245693 A1 | 9/2013 | Euteneuer et al. |
| 2013/0245706 A1 | 9/2013 | Euteneuer et al. |
| 2013/0245707 A1 | 9/2013 | Euteneuer et al. |
| 2013/0245762 A1 | 9/2013 | Van Kampen et al. |
| 2013/0245774 A1 | 9/2013 | Euteneuer et al. |

FOREIGN PATENT DOCUMENTS

| | | |
|---|---|---|
| EP | 0298400 A1 | 1/1989 |
| EP | 0390613 A1 | 10/1990 |
| EP | 0543499 A1 | 5/1993 |
| EP | 0548998 A1 | 6/1993 |
| EP | 0557963 A1 | 9/1993 |
| EP | 0589306 A2 | 3/1994 |
| EP | 0908152 A1 | 4/1999 |
| EP | 1491157 A1 | 12/2004 |
| EP | 1559379 A1 | 8/2005 |
| EP | 2030576 A2 | 3/2009 |
| GB | 2154688 A | 9/1985 |
| GB | 2397240 A | 7/2004 |
| WO | WO 85/05025 | 11/1985 |
| WO | WO 01/76456 A2 | 10/2001 |
| WO | WO 02/34140 A2 | 5/2002 |
| WO | WO 03/105670 A2 | 12/2003 |
| WO | WO 04/000138 A1 | 12/2003 |
| WO | WO 2004/093690 A1 | 11/2004 |
| WO | WO 2005/016389 A2 | 2/2005 |
| WO | WO 2006/086679 A1 | 8/2006 |
| WO | WO 2007/014910 A1 | 2/2007 |
| WO | WO 2007/030676 A2 | 3/2007 |
| WO | WO 2007/078978 A2 | 7/2007 |
| WO | WO 2007/082088 A2 | 7/2007 |

(56) References Cited

FOREIGN PATENT DOCUMENTS

| WO | WO 2008/111073 A2 | 9/2008 |
| WO | WO 2008/111078 A2 | 9/2008 |
| WO | WO 2008/139473 A2 | 11/2008 |
| WO | WO 2009/079211 A1 | 6/2009 |
| WO | WO 2009/143331 A1 | 11/2009 |
| WO | WO 2011/095890 A2 | 8/2011 |
| WO | WO 2011/128903 A2 | 10/2011 |

OTHER PUBLICATIONS

Bahler et al., "Trabecular bypass stents decrease intraocular pressure in cultured himan anterior segments," Am. J. Ophthalmology; vol. 138; No. 6; pp. 988-994; Dec. 2004.

Chamay et al., "Digital contracture deformity after implantation of a silicone prosthesis: Light and electron microscopic study," The Journal of Hand Surgery; vol. 3; No. 3; pp. 266-270; May 1978.

D'Ermo et al., "Our results with the operation of ab externo," Ophthalmologica; vol. 168; pp. 347-355; 1971.

France et al., "Biomechanical evaluation of rotator cuff fixation methods," The American Journal of Sports Medicine; vol. 17; No. 2; 1989.

Goodship et al., "An assessment of filamentous carbon fibre for the treatment of tendon injury in the horse," Veterinary Record; vol. 106; pp. 217-221; Mar. 8, 1980.

Hunter et al., "Flexor-tendon reconstruction in severely damaged hands," The Journal of Bone and Joint Surgery (American Volume); vol. 53-A; No. 5; pp. 329-358; Jul. 1971.

Johnstone et al., "Microsurgery of Schlemm's canal and the human aqueous outflow system," Am. J. Ophthalmology; vol. 76; No. 6; pp. 906-917; Dec. 1973.

Kowalsky et al., "Evaluation of suture abrasion against rotator cuff tendon and proximal humerus bone," Arthroscopy: The Journal of Arthroscopic and Related Surgery; vol. 24; No. 3; pp. 329-334; Mar. 2008.

Lee et al., "Aqueous-venous and intraocular pressure. Preliminary report of animal studies," Investigative Ophthalmology; vol. 5; No. 1; pp. 59-64; Feb. 1966.

Maepea et al., "The pressures in the episcleral veins, Schlemm's canal and the trabecular meshwork in monkeys: Effects of changes in intraocular pressure," Exp. Eye Res.; vol. 49; pp. 645-663; 1989.

Nicolle et al., "A silastic tendon prosthesis as an adjunct to flexor tendon grafting: An experimental and clinical evaluation," British Journal of Plastic Surgery; vol. 22; Issues 3-4; pp. 224-236; 1969.

Rubin et al., "The use of acellular biologic tissue patches in foot and ankle surgery," Clinics in Podiatric Medicine and Surgery; No. 22; pp. 533-552; 2005.

Schultz, "Canaloplasty procedure shows promise for open-angle glaucoma in European stud," Ocular Surgery News; pp. 34-35; Mar. 1, 2007.

Spiegel et al., "Schlemm's canal implant: A new method to lower intraocular pressure in patients with POAG," Ophthalmic Surgery and Lasers; vol. 30; No. 6; pp. 492-494; Jun. 1999.

Stetson et al., "Arthroscopic treatment of partial rotator cuff tears," Operative Techniques in Sports Medicine (Apr. 2004) 12 (2): 135-148.

Valdez et al., "Repair of digital flexor tendon lacerations in the horse, using carbon fiber implants," JAYMA; vol. 177; No. 5; pp. 427-435; Sep. 1, 1980.

Wikipedia, the free encyclopedia, "Rotator cuff tear," <http://en.wikipedia.org/wiki/Rotator_cuff_tear> on Dec. 6, 2012; 14 pages.

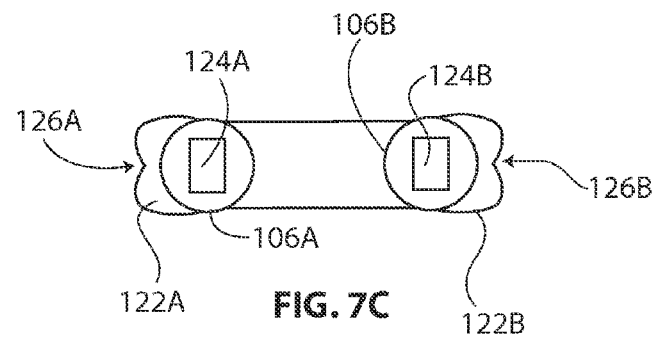
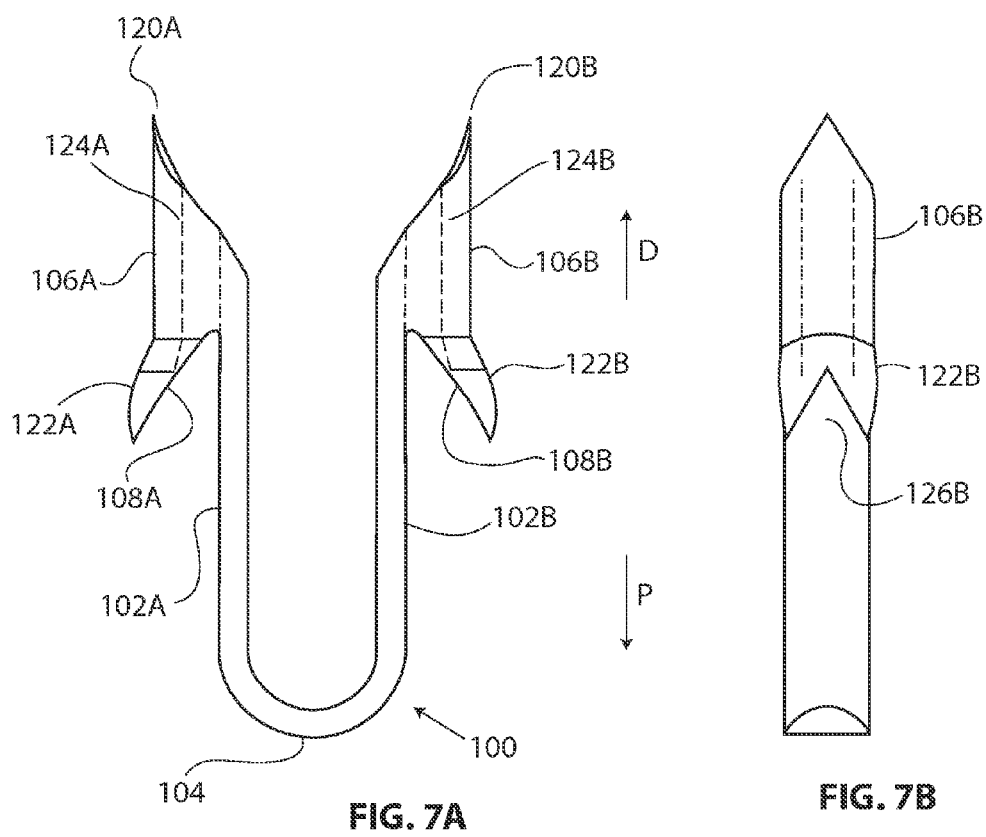
FIG. 7C
FIG. 7A
FIG. 7B

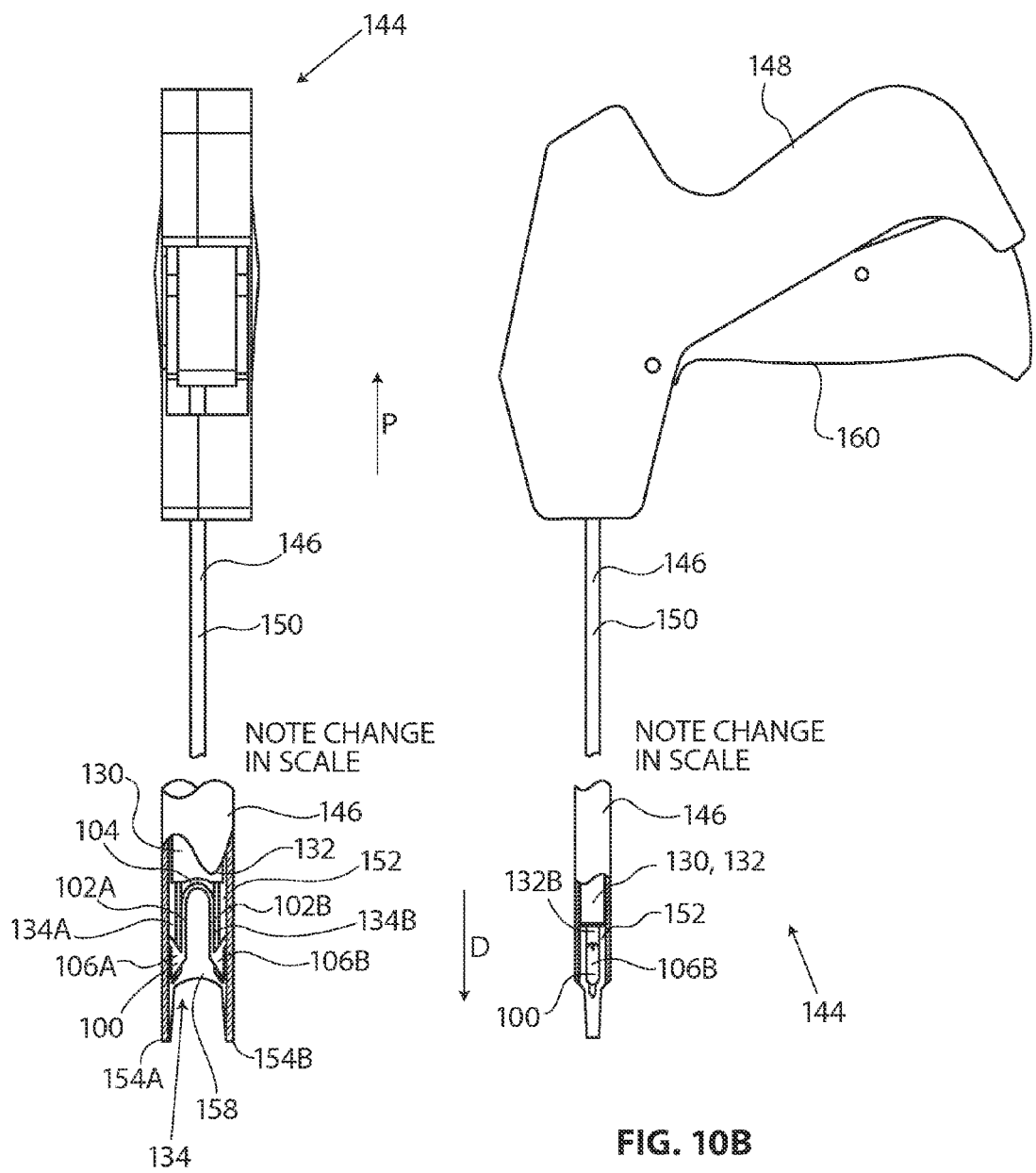

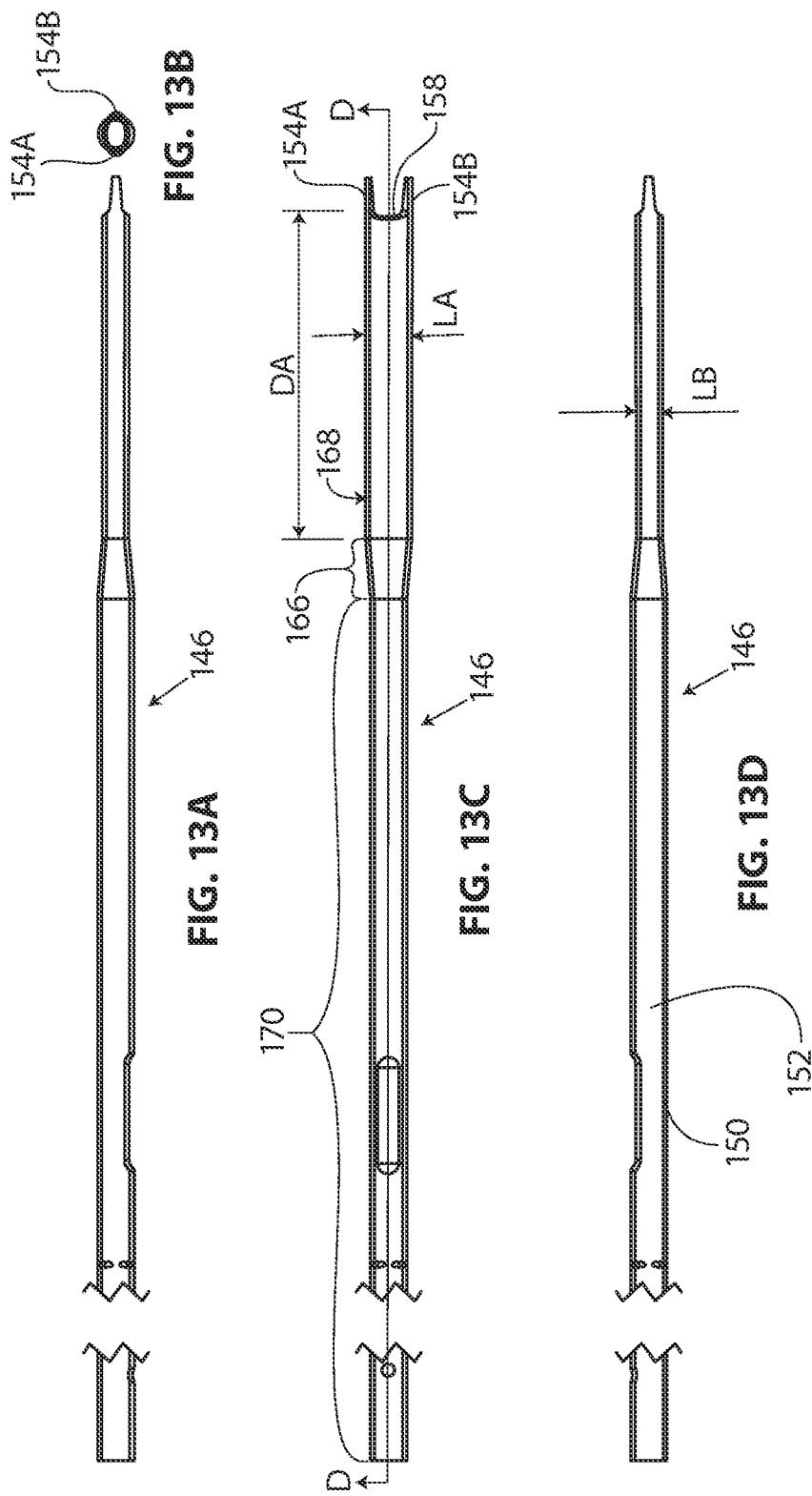

METHODS AND APPARATUS FOR FIXING SHEET-LIKE MATERIALS TO A TARGET TISSUE

CROSS REFERENCE TO RELATED APPLICATIONS

The present application is a continuation application of U.S. application Ser. No. 12/794,540, filed on Jun. 4, 2010, which claims the benefit of U.S. Provisional Patent application No. 61/313,051 filed on Mar. 11, 2010; U.S. Provisional Patent application No. 61/253,800 filed on Oct. 21, 2009; and U.S. Provisional application No. 61/184,198 filed on Jun. 4, 2009; and which applications are incorporated herein by reference. A claim of priority to all, to the extent appropriate, is made.

All publications and patent applications mentioned in this specification are herein incorporated by reference to the same extent as if each individual publication or patent application was specifically and individually indicated to be incorporated by reference.

FIELD OF THE INVENTION

The present invention relates generally to orthopedic medicine and surgery. More particularly, the present invention relates to methods and apparatus for delivery and fixation of sheet-like materials, such as for treating articulating joints.

BACKGROUND OF THE INVENTION

The glenohumeral joint of the shoulder is found where the head of the humerus mates with a shallow depression in the scapula. This shallow depression is known as the glenoid fossa. Six muscles extend between the humerus and scapula and actuate the glenohumeral joint. These six muscles include the deltoid, the teres major, and the four rotator cuff muscles. As disclosed by Ball et al. in U.S. Patent Publication No. US 2008/0188936 . mu.1 and as illustrated in FIG. 1 the rotator cuff muscles are a complex of four muscles. These four muscles are the supraspinatus, the infraspinatus, the subscapularis, and the teres minor. The centering and stabilizing roles played by the rotator cuff muscles are critical to the proper function of the shoulder. The rotator cuff muscles provide a wide variety of moments to rotate the humerus and to oppose unwanted components of the deltoid and pectoralis muscle forces.

The four muscles of the rotator cuff arise from the scapula 12. The distal tendons of the rotator cuff muscles splay out and interdigitate to form a common continuous insertion on the humerus 14. The subscapularis 16 arises from the anterior aspect of the scapula 12 and attaches over much of the lesser tuberosity of the humerous. The supraspinatus muscle 18 arises from the supraspinatus fossa of the posterior scapula, passes beneath the acromion and the acromioclavicular joint, and attaches to the superior aspect of the greater tuberosity 11. The infraspinatus muscle 13 arises from the infraspinous fossa of the posterior scapula and attaches to the posterolateral aspect of the greater tuberosity 11. The teres minor 15 arises from the lower lateral aspect of the scapula 12 and attaches to the lower aspect of the greater tuberosity 11.

The mechanics of the rotator cuff muscles 10 are complex. The rotator cuff muscles 10 rotate the humerus 14 with respect to the scapula 12, compress the humeral head 17 into the glenoid fossa providing a critical stabilizing mechanism to the shoulder (known as concavity compression), and provide muscular balance. The supraspinatus and infraspinatus provide 45 percent of abduction and 90 percent of external rotation strength. The supraspinatus and deltoid muscles are equally responsible for producing torque about the shoulder joint in the functional planes of motion.

The rotator cuff muscles 10 are critical elements of this shoulder muscle balance equation. The human shoulder has no fixed axis. In a specified position, activation of a muscle creates a unique set of rotational moments. For example, the anterior deltoid can exert moments in forward elevation, internal rotation, and cross-body movement. If forward elevation is to occur without rotation, the cross-body and internal rotation moments of this muscle must be neutralized by other muscles, such as the posterior deltoid and infraspinatus. The timing and magnitude of these balancing muscle effects must be precisely coordinated to avoid unwanted directions of humeral motion. Thus the simplified view of muscles as isolated motors, or as members of force couples must give way to an understanding that all shoulder muscles function together in a precisely coordinated way—opposing muscles canceling out undesired elements leaving only the net torque necessary to produce the desired action. Injury to any of these soft tissues can greatly inhibit ranges and types of motion of the arm.

With its complexity, range of motion and extensive use, a fairly common soft tissue injury is damage to the rotator cuff or rotator cuff tendons. Damage to the rotator cuff is a potentially serious medical condition that may occur during hyperextension, from an acute traumatic tear or from overuse of the joint. With its critical role in abduction, rotational strength and torque production, the most common injury associated with the rotator cuff region is a strain or tear involving the supraspinatus tendon. A tear in the supraspinitus tendon 19 is schematically depicted in FIG. 2. A tear at the insertion site of the tendon with the humerus, may result in the detachment of the tendon from the bone. This detachment may be partial or full, depending upon the severity of the injury. Additionally, the strain or tear can occur within the tendon itself. Injuries to the supraspinatus tendon 19 and recognized modalities for treatment are defined by the type and degree of tear. The first type of tear is a full thickness tear as also depicted in FIG. 2, which as the term indicates is a tear that extends through the thickness of the supraspinatus tendon regardless of whether it is completely torn laterally. The second type of tear is a partial thickness tear which is further classified based on how much of the thickness is torn, whether it is greater or less than 50% of the thickness.

The accepted treatment for a full thickness tear or a partial thickness tear greater than 50% includes reconnecting the torn tendon via sutures. For the partial thickness tears greater than 50%, the tear is completed to a full thickness tear by cutting the tendon prior to reconnection. In contrast to the treatment of a full thickness tear or a partial thickness tear of greater than 50%, the treatment for a partial thickness tear less than 50% usually involves physical cessation from use of the tendon, i.e., rest. Specific exercises can also be prescribed to strengthen and loosen the shoulder area. In many instances, the shoulder does not heal and the partial thickness tear can be the source of chronic pain and stiffness. Further, the pain and stiffness may cause restricted use of the limb which tends to result in further degeneration or atrophy in the shoulder. Surgical intervention may be required for a partial thickness tear of less than 50%, however, current treatment interventions do not include repair of the tendon, rather the surgical procedure is directed to arthroscopic removal of bone to relieve points of impingement or create a larger tunnel between the tendon and bone that is believed to be causing tendon damage. As part of the treatment, degenerated tendon may also be removed using a debridement procedure in which tendon material is ablated. Again, the tendon partial tear is not repaired. Several authors have reported satisfactory early post operative results from these procedures, but over time recurrent symptoms have been noted. In the event of recurrent symptoms, many times a patient will "live with the pain". This may result in less use of the arm and shoulder which further causes degeneration of the tendon and may lead to more extensive damage. A tendon repair would then need to be done in a later procedure if the prescribed treatment for partial tear was unsuccessful in relieving pain and stiffness or over time the tear propagated through injury or degeneration to a full thickness tear or a partial thickness tear greater than 50% with attendant pain and debilitation. A subsequent later procedure would include the more drastic procedure of completing the tear to full thickness and suturing the ends of the tendon back together. This procedure requires extensive rehabilitation, has relatively high failure rates and subjects the patient who first presented and was treated with a partial thickness tear less than 50% to a second surgical procedure.

As described above, adequate treatments do not currently exist for repairing a partial thickness tear of less than 50% in the supraspinatus tendon. Current procedures attempt to alleviate impingement or make room for movement of the tendon to prevent further damage and relieve discomfort but do not repair or strengthen the tendon. Use of the still damaged tendon can lead to further damage or injury. Prior damage may result in degeneration that requires a second more drastic procedure to repair the tendon. Further, if the prior procedure was only partially successful in relieving pain and discomfort, a response may be to use the shoulder less which leads to degeneration and increased likelihood of further injury along with the need for more drastic surgery. There is a large need for surgical techniques and systems to treat partial thickness tears of less than 50% and prevent future tendon damage by strengthening or repairing the native tendon having the partial thickness tear.

SUMMARY OF THE INVENTION

In accordance with aspects of the present invention, a staple for attaching a sheet-like implant to tissue or bone is disclosed. In some embodiments, the staple includes first and second arms, and first and second flukes. The first arm has a proximal end and a distal end, and the second arm has a proximal end and a distal end. A bridge extends from the proximal end of the first arm to the proximal end of the second arm. The first fluke has a proximal end abutting the distal end of the first arm, and the first fluke extends distally from the first arm. The first fluke has a lateral extent larger than a lateral extent of the first arm and is mounted eccentrically thereto. The first fluke includes a proximal surface projecting at an outward angle in a proximal direction away from the distal end of the first arm to engage the tissue or bone when inserted therein. This arrangement causes the first fluke to rotate in response to a pullout force on the bridge. The second fluke has a proximal end abutting the distal end of the second arm and extends distally. The second fluke has a lateral extent larger than the lateral extent of the second arm and is mounted eccentrically thereto. The second fluke includes a proximal surface projecting at an outward angle in a proximal direction and away from the second arm near the proximal end of the second fluke to engage the tissue or bone when inserted therein. This arrangement causes the second fluke to rotate in response to a pullout force on the bridge.

In some embodiments of the invention, the lateral extent of each of the flukes is at least about three times the lateral extent of the arm adjacent thereto. In some embodiments, the lateral extent of the first arm and the second arm is about 0.3 mm. to about 3.0 mm.

Each of the first fluke and the second fluke may include a lumen extending from the proximal end to the distal end thereof. The lumen may be spaced laterally from the respective arm mounted thereto. In some embodiments, each lumen of the first and the second fluke is sized to receive a first stake and a second stake, respectively, of a staple delivery device therethrough. The first fluke may include a proximal surface that engages the first stake and the second fluke may include a proximal surface that engages the second stake to receive pushing forces for inserting the staple into the tissue.

In some embodiments, at least a portion of each of the lengths of the first and the second arms is flexible to allow flexing of the first and second flukes relative thereto. This arrangement is designed to achieve rotational engagement of each fluke to the tissue or bone.

According to aspects of the invention, the first arm, second arm, first fluke, second fluke, proximal surfaces and bridge may be integrally formed of a polymeric material. In some embodiments, the polymeric material is bioresorbable.

According to other aspects of the invention, methods for attaching a sheet-like implant to a target tissue are disclosed. In some embodiments, the method includes the steps of providing a staple, creating first and second pilot holes in the target tissue, and advancing parts of the staple into the pilot holes. In these embodiments, the staple includes first and second arms, each having proximal and distal ends. A bridge extends from the proximal end of the first arm to the proximal end of the second arm. The staple further includes a first fluke and a second fluke. The first fluke has a proximal end abutting the distal end of the first arm. The first fluke also extends distally from the first arm, has a lateral extent larger than a lateral extent of the first arm, and is mounted eccentrically thereto. The first fluke includes a proximal surface projecting at an outward angle in a proximal direction away from the distal end of the first arm. The second fluke has a proximal end abutting the distal end of the second arm. The second fluke also extends distally from the second arm, has a lateral extent larger than a lateral extent of the second arm, and is mounted eccentrically thereto. The second fluke includes a proximal surface projecting at an outward angle in a proximal direction away from the distal end of the second arm.

In the advancing step of the above methods, the first fluke of the staple is advanced into the first pilot hole and the second fluke is advanced into the second pilot hole, such that the bridge portion of the staple extends from adjacent the first pilot hole to adjacent the second pilot hole.

In some of the inventive methods, a first force is applied to a surface of the first fluke to produce a first moment. The first moment causes the first fluke to rotate in a first direction so that a first longitudinal axis of the first fluke is skewed relative to a central axis of the first pilot hole. A second force is also applied to a surface of the second fluke to produce a second moment. The second moment causes the second fluke to rotate in a second direction so that a second longitudinal axis of the second fluke is skewed relative to a central axis of the second pilot hole. The first moment has a first direction and the second moment has a second direction. The first and the second forces may be applied simultaneously. In some embodiments, the first force is applied to the proximal surface of the first fluke at a location that is offset from the first arm, and the second force is applied to the proximal surface of the second fluke at a location that is offset from the second arm.

In some of the above embodiments, the application of the first force and the second force place the first arm, the second arm, and the bridge in tension relative to the tissue. This aids in staple retention as the first and the second fluke engage the tissue. In some embodiments, the first arm provides a first reaction force in response to the first force and the second force. The first reaction force has a first reaction direction that is generally opposite the direction of the first force. In these embodiments, the first reaction direction is offset from the direction of the first force. In some of the above embodiments, the second arm provides a second reaction force in response to the first force and the second force. The second reaction force has a second reaction direction that is generally opposite the direction of the second force. In these embodiments, the second reaction direction is offset from the direction of the second force.

In some embodiments, a force is applied to the first and second fluke to place the first arm, the second arm, and the bridge in tension relative to the tissue to aid in staple retention as the first and the second fluke engage the tissue. In some embodiments, releasing the force applied to the first and second flukes allows the tissue to apply a force against the staple. This causes the first and second flukes to further engage the tissue to inhibit staple pullout. The force of the tissue against the staple may cause the first fluke to rotate in a first direction so that a first longitudinal axis of the first fluke is skewed relative to a central axis of the first pilot hole. It may also cause the second fluke to rotate in a second direction so that a second longitudinal axis of the second fluke is skewed relative to a central axis of the second pilot hole. In some embodiments, the first and second directions are opposite.

In some embodiments, at least one of the first and the second pilot holes is created in the sheet-like implant and the target tissue. At least a part of the bridge portion of the staple will contact the sheet-like implant after the first and the second flukes of the staple have been advanced into the first and the second pilot holes.

Additional aspects of the present invention will become clear after review of the Detailed Description with reference to the following drawings.

BRIEF DESCRIPTION OF THE DRAWINGS

FIG. 7A, FIG. 7B, and FIG. 7C are multiple plan views illustrating an exemplary staple in accordance with the present detailed description.

FIG. 10A and FIG. 10B illustrate multiple plan views of an exemplary fixation tool in accordance with the present detailed description.

FIG. 13A, FIG. 13B, FIG. 13C and FIG. 13D are multiview projections illustrating a fixation tool shaft shown in the previous Figures.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

As used herein, the term "tissue" refers to soft tissue, such as a tendon, and/or bone tissue, depending on the context in which it is used.

Figure 1:
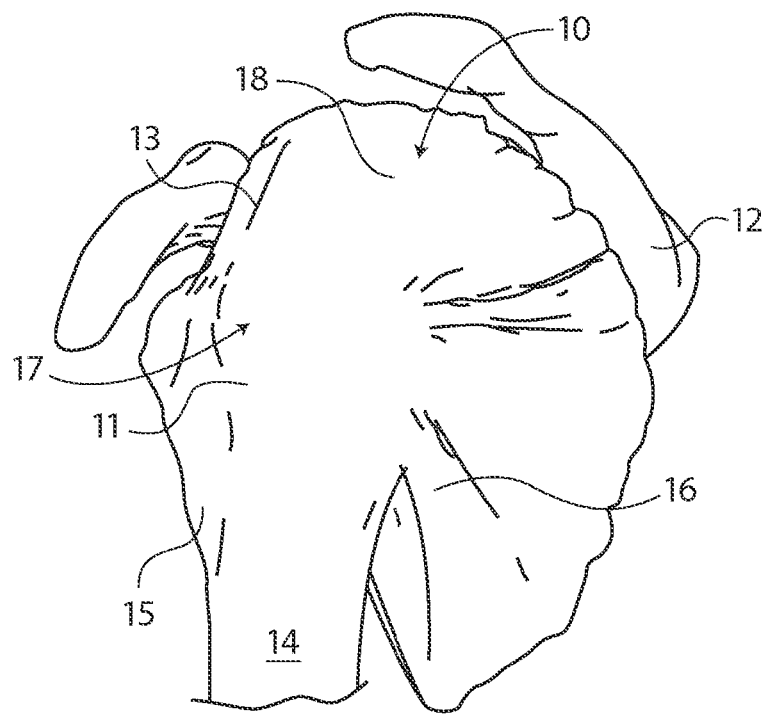
FIG. 1 is a simplified perspective view of the human rotator cuff and associated anatomical structure.
Figure 2:
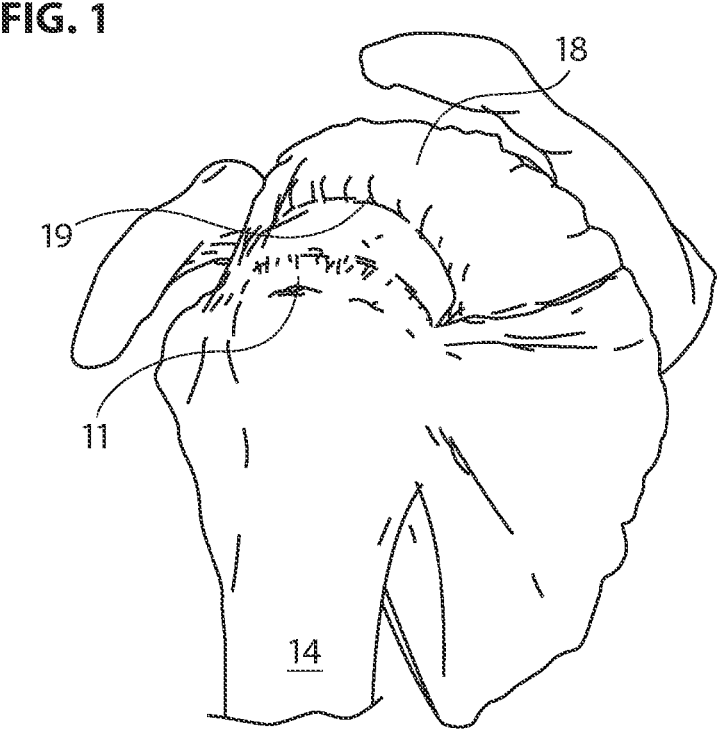
FIG. 2 is a schematic depiction of a full thickness tear in the supraspinatus tendon of the rotator cuff of FIG. 1.
Figure 3:
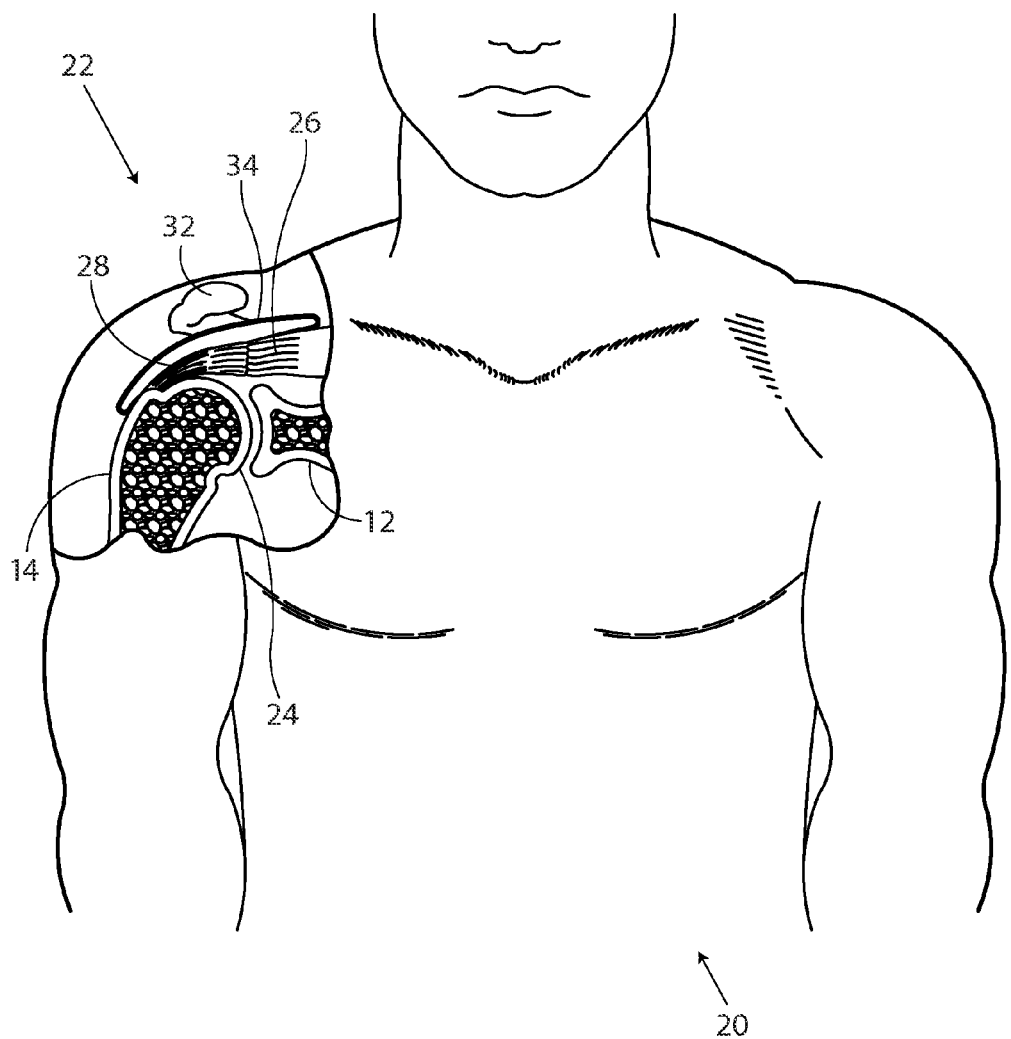
FIG. 3 is a stylized anterior view of a patient with a shoulder of patient being shown in cross-section for purposes of illustration.

FIG. 3 is a stylized anterior view of a patient 20. For purposes of illustration, a shoulder 22 of patient 20 is shown in cross-section in FIG. 3. Shoulder 22 includes a humerus 14 and a scapula 12. In FIG. 3, a head 24 of humerus 14 can be seen mating with a glenoid fossa of scapula 12 at a glenohumeral joint. With reference to FIG. 3, it will be appreciated that the glenoid fossa comprises a shallow depression in scapula 12. The movement of humerus 14 relative to scapula 12 is controlled by a number of muscles including: the deltoid, the supraspinatus, the infraspinatus, the subscapularis, and the teres minor. For purposes of illustration, only the supraspinatus 26 is shown in FIG. 3.

With reference to FIG. 3, it will be appreciated that a distal tendon 28 of the supraspinatus 26 meets humerus 14 at an insertion point. Scapula 12 of shoulder 22 includes an acromium 32. In FIG. 3, a subacromial bursa 34 is shown extending between acromium 32 of scapula 12 and head 24 of humerus 14. In FIG. 3, subacromial bursa 34 is shown overlaying supraspinatus 26. Subacromial bursa 34 is one of the hundreds of bursae found the human body. Each bursa comprises a fluid filled sac. The presence of these bursae in the body reduces friction between bodily tissues. Injury and/or infection of the bursa can cause it to become inflamed. This condition is sometimes referred to as bursitis.

The exemplary methods and apparatus described herein may be used to fix tendon repair implants to various target tissues. For example, a tendon repair implant may be fixed to one or more tendons associated with an articulating joint, such as the glenohumeral joint. The tendons to be treated may be torn, partially torn, have internal micro-tears, be untorn, and/or be thinned due to age, injury or overuse. Applicants believe that the methods and apparatus of the present application and related devices may provide very beneficial therapeutic effect on a patient experiencing joint pain believed to be caused by partial thickness tears and/or internal microtears. By applying a tendon repair implant early before a full tear or other injury develops, the implant may cause the tendon to thicken and/or at least partially repair itself, thereby avoiding more extensive joint damage, pain, and the need for more extensive joint repair surgery.

Figure 4:
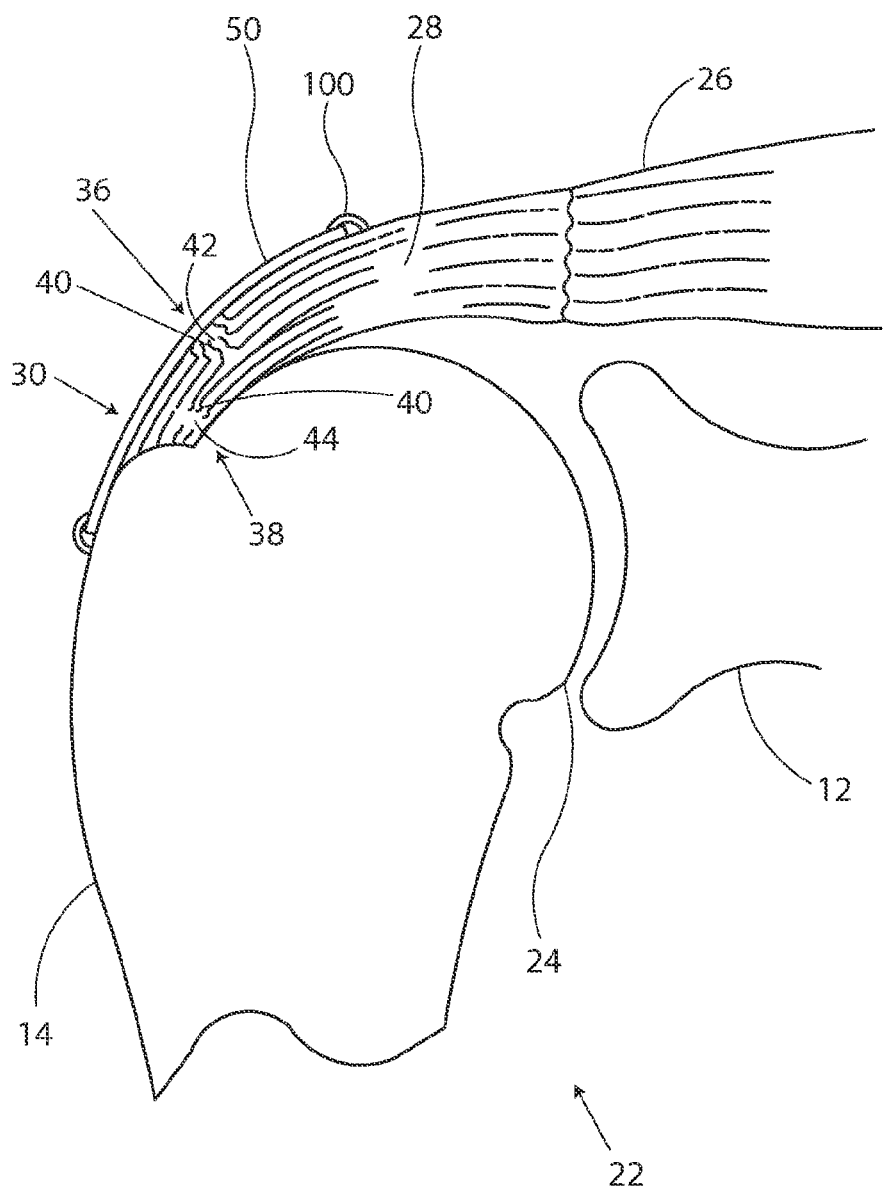
FIG. 4 is a stylized anterior view of a shoulder including a humerus and a scapula. The head of the humerus is shown mating with the glenoid fossa of the scapula at a glenohumeral joint and a sheet-like material is fixed to the tendon.

FIG. 4 is a stylized anterior view of a shoulder 22 including a humerus 14 and a scapula 12. In FIG. 4, a head 24 of humerus 14 is shown mating with a glenoid fossa of scapula 12 at a glenohumeral joint. A supraspinatus 26 is also shown in FIG. 4. This muscle (along with others) control the movement of humerus 14 relative to scapula 12. A distal tendon 28 of supraspinatus 26 meets humerus 14 at an insertion point 30.

In the embodiment of FIG. 4, distal tendon 28 includes a first damaged portion 36. A number of loose tendon fibers 40 in first damaged portion 36 are visible in FIG. 4. First damaged portion 36 includes a first tear 42 extending partially through distal tendon 28. First tear 42 may therefore be referred to as a partial thickness tear. With reference to FIG. 4, it will be appreciated that first tear 42 begins on the side of distal tendon 28 facing the subacromial bursa (shown in the previous Figure) and ends midway through distal tendon 28. Accordingly, first tear 42 may be referred to as a bursal side tear.

With reference to FIG. 4, it will be appreciated that distal tendon 28 includes a second damaged portion 38 located near insertion point 30. in the embodiment of FIG. 4, second damaged portion 38 of distal tendon 28 has become frayed and a number of loose tendon fibers 40 are visible in FIG. 4. Second damaged portion 38 of distal tendon 28 includes second tear 44. With reference to FIG. 4, it will be appreciated that second tear 44 begins on the side of distal tendon 28 facing the humerus 14. Accordingly, second damaged portion 38 may be referred to as an articular side tear.

In the embodiment of FIG. 4, a sheet-like implant 50 has been placed over the bursal side of distal tendon 28. With reference to FIG. 4, it will be appreciated that sheet-like implant 50 extends over insertion point 30, first tear 42 and second tear 44. Some useful methods in accordance with this detailed description may include placing a tendon repair implant on the bursal side of a tendon regardless of whether the tears being treated are on the bursal side, articular side or within the tendon. In some cases the exact location and nature of the tears being treated may be unknown. A tendon repair implant may be applied to the bursal side of a tendon to treat shoulder pain that is most likely caused by one or more partial thickness tears in the tendon. In the embodiment of FIG. 4, sheet-like implant 50 is fixed to distal tendon 28 and to humerus 14 by a plurality of staples 100 as described herein in detail.

Figure 5:
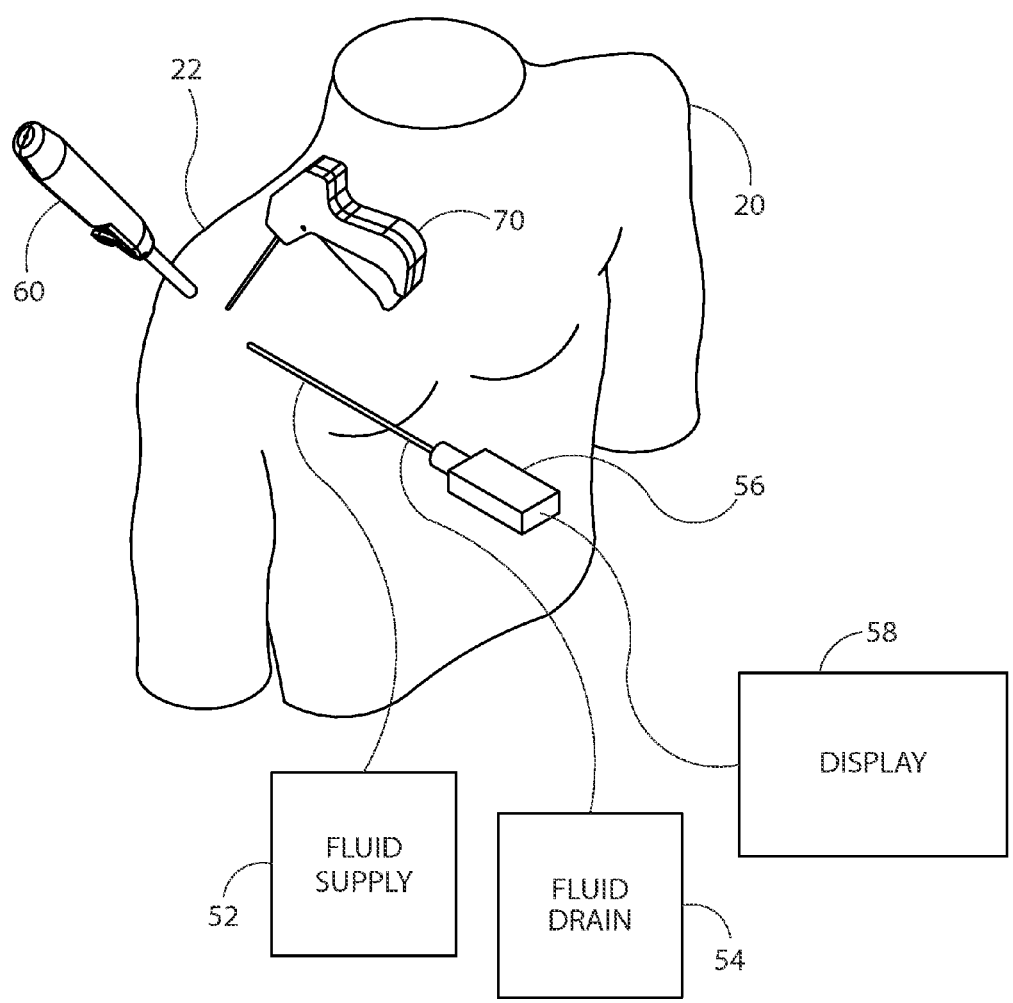
FIG. 5 is a stylized perspective view illustrating an exemplary procedure for treating a shoulder of a patient.

FIG. 5 is a stylized perspective view illustrating an exemplary procedure for treating a shoulder 22 of a patient 20. The procedure illustrated in FIG. 5 may include, for example, fixing tendon repair implants to one or more tendons of shoulder 22. The tendons treated may be torn, partially torn, have internal micro-tears, be untorn, and/or be thinned due to age, injury or overuse.

Shoulder 22 of FIG. 5 has been inflated to create a cavity therein. In the exemplary embodiment of FIG. 5A, a fluid supply 52 is pumping a continuous flow of saline into the cavity. This flow of saline exits the cavity via a fluid drain 54. A camera 56 provides images from inside the cavity. The images provided by camera 56 may be viewed on a display 58.

Camera 56 may be used to visually inspect the tendons of shoulder 22 for damage. A tendon repair implant in accordance with this disclosure may be fixed to a bursal surface of the tendon regardless of whether there are visible signs of tendon damage. Applicants believe that the methods and apparatus of the present application and related devices may provide very beneficial therapeutic effect on a patient experiencing joint pain believed to be caused by internal microtears, but having no clear signs of tendon tears. By applying a tendon repair implant early before a full tear or other injury develops, the implant may cause the tendon to thicken and/or at least partially repair itself, thereby avoiding more extensive joint damage, pain, and the need for more extensive joint repair surgery.

A delivery system 60 can be seen extending from shoulder 22 in FIG. 5. Delivery system 60 comprises a sheath that is fixed to a handle. The sheath defines a lumen and a distal opening fluidly communicating the lumen. In the embodiment of FIG. 5, the distal opening of the sheath has been placed in fluid communication with the cavity created in shoulder 22.

A tendon repair implant is at least partially disposed in the lumen defined by the sheath of delivery system 60. Delivery system 60 can be used to place the tendon repair implant inside shoulder 22. Delivery system 60 can also be used to hold the tendon repair implant against the tendon. In some embodiments, the tendon repair implant is folded into a compact configuration when inside the lumen of the sheath. When this is the case, delivery system 60 may be used to unfold the tendon repair implant into an expanded shape.

The tendon repair implant may be fixed to the tendon while it is held against the tendon by delivery system 60. Various attachment elements may be used to fix the tendon repair implant to the tendon. Examples of attachment elements that may be suitable in some applications include sutures, tissue anchors, bone anchors, and staples. In the exemplary embodiment of FIG. 5, the shaft of a fixation tool 70 is shown extending into shoulder 22. In one exemplary embodiment, fixation tool 70 is capable of fixing the tendon repair implant to the tendon with one or more staples while the tendon repair implant is held against the tendon by delivery system 60.

Figure 6:
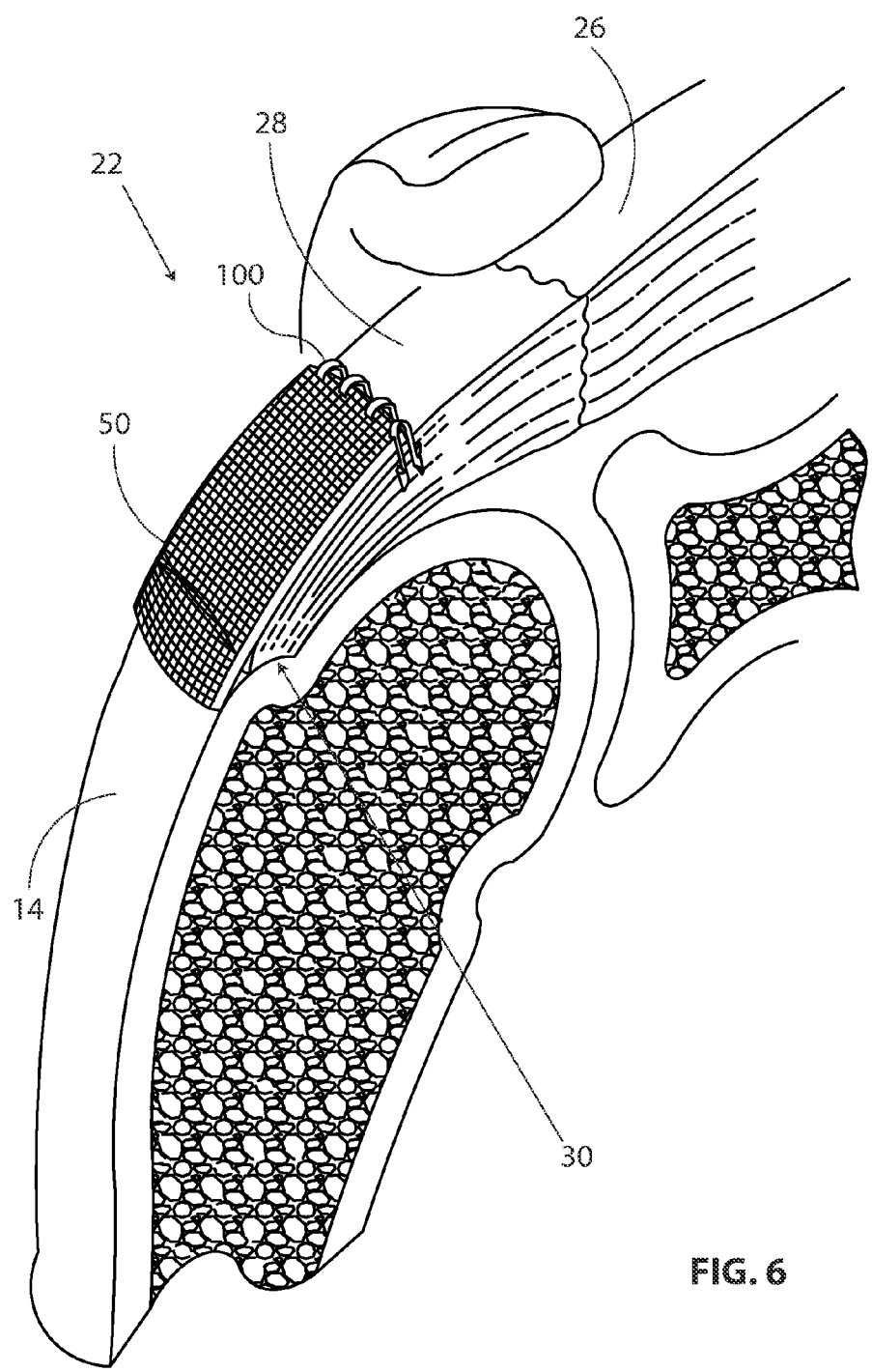
FIG. 6 is a stylized perspective view of a shoulder including a supraspinatus having a distal tendon with a sheet-like material fixed thereto. A proximal end of the supraspinatus is fixed to the scapula and the distal tendon of the supraspinatus is fixed to the humerus.

FIG. 6 is a stylized perspective view of a shoulder 22 including a supraspinatus 26 having a distal tendon 28. With reference to FIG. 6, it will be appreciated that a tendon repair implant 50 has been fixed to a surface of distal tendon 28. Tendon repair implant 50 may comprise, for example, various sheet-like structures without deviating from the spirit and scope of the present detailed description. In some useful embodiments, the sheet-like structure may comprise a plurality of fibers. The fibers may be interlinked with one another. When this is the case, the sheet-like structure may comprise a plurality of apertures comprising the interstitial spaces between fibers. Various processes may be used to interlink the fibers with one another. Examples of processes that may be suitable in some applications including weaving, knitting, and braiding.

In some embodiment, the sheet-like structure may comprise a laminate including multiple layers of film with each layer of film defining a plurality of micro-machined or formed holes. The sheet-like structure of the tendon repair implant may also comprise a plurality of electro-spun nanofiber filaments forming a composite sheet. Additionally, the sheet-like structure may comprise a synthetic sponge material that defines a plurality of pores. The sheet-like structure may also comprise a reticulated foam material. Reticulated foam materials that may be suitable in some applications are available from Biomerix Corporation of Freemont, Calif. which identifies these materials using the trademark BIOMATERIAL™

Various attachment elements may be used to fix tendon repair implant 50 to distal tendon 28 without deviating from the spirit and scope of this detailed description. Examples of attachment elements that may be suitable in some applications include sutures, tissue anchors, bone anchors, and staples. In the exemplary embodiment of FIG. 6, a plurality of staples 100 are fixing tendon repair implant 50 to distal tendon 28. In some exemplary methods, a plurality of staples 100 may be applied using a fixation tool. The fixation tool may then be withdrawn from the body of the patient. Distal tendon 28 meets humerus 14 at an insertion point 30. With reference to FIG. 6, it will be appreciated that sheet-like implant 50 extends over insertion point 30. Tendon repair implant may be applied to distal tendon 28, for example, using the procedure illustrated in the previous Figure.

FIG. 7A, FIG. 7B, and FIG. 7C are multiple plan views illustrating an exemplary staple 100 in accordance with the present detailed description. FIG. 7A, FIG. 7B, and FIG. 7C may be collectively referred to as FIG. 7. A proximal direction is illustrated with an arrow P in FIG. 7. A distal direction is illustrated with a second arrow D in FIG. 7.

Staple 100 comprises a first arm 102A, a second arm 102B, and a bridge 104 extending from the proximal end of first arm 102A to the proximal end of second arm 102B. The distal end of first arm 102A abuts the proximal end of a first fluke 106A. Similarly, the distal end of second arm 102B abuts the proximal end of a second fluke 106B. In FIG. 7, first fluke 106A and second fluke 106B are shown extending distally from first arm 102A and second arm 102B, respectively. With reference to FIG. 7, it will be appreciated that first fluke 106A has a lateral extent that is larger than a lateral extent of first arm 102A. First fluke 106A is mounted eccentrically to first arm 102A in the embodiment of FIG. 7. Second fluke 106B is mounted eccentrically to second arm 102B and second fluke 106B has a lateral extent that is larger than a lateral extent of second arm 102B. First fluke 106A includes a first proximal surface 108A projecting at an outward angle in a proximal direction away from the distal end of first arm 102A. Second fluke 106B includes a second proximal surface 108B projecting at an outward angle in a proximal direction away from the distal end of second arm 102B.

With reference to FIG. 7A, it will be appreciated that first fluke 106A includes a first point 120A and a first barb 122A. Second fluke 106B includes a second point 120B and a second barb 122B. In FIG. 7, first point 120A and second point 120B are shown generally pointing in the distal direction indicated by arrow D. Also in FIG. 7, first barb 122A and second barb 122B are shown generally pointing in the proximal direction indicated by arrow P.

With reference to FIG. 7A it will be appreciated that first fluke 106A defines a first passageway 124A and second fluke 106B defines a second passageway 124B. In the exemplary embodiment of FIG. 7, first passageway 124A extends through first fluke 106A and second passageway 124B extends through second fluke 106B. It will be appreciated, however, that first passageway 124A may extend through other portions of staple 100 in some embodiments. Similarly, second passageway 124B may extend through other portions of staple 100 in some embodiments. With reference to FIG. 7B it will be appreciated that, first passageway 124A and second passageway 124B each have a generally square cross-sectional shape. It will be appreciated, however, that first passageway 124A and second passageway 124B may have various cross-sectional shapes without deviating from the spirit and scope of the present detailed description. Further, each passageway can extend partially through the length of each fluke rather than all the way through to provide a cavity rather than a passageway.

With reference to FIG. 7C, it will be appreciated that first barb 122A of first fluke 106A defines a first notch 126A. In the exemplary embodiment of FIG. 7, first notch 126A divides first barb 122A into a first sub-barb and a second sub-barb. Second barb 122B of second fluke 106B defines a second notch 126B. In the exemplary embodiment of FIG. 7, second notch 126B divides second barb 122B into a first sub-barb and a second sub-barb.

Figure 8:
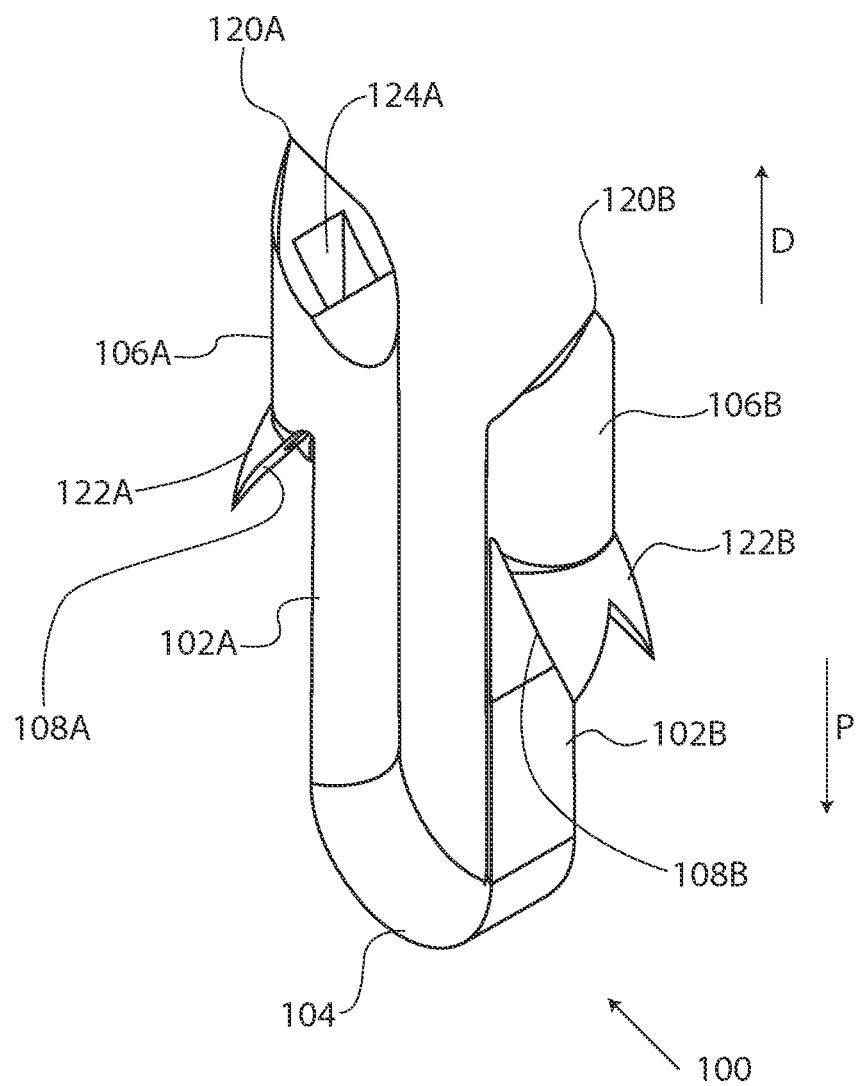
FIG. 8 is a perspective view further illustrating the staple shown in the previous Figure.

FIG. 8 is a perspective view showing staple 100 shown in the previous Figure. Staple 100 comprises a first arm 102A, a second arm 102B, and a bridge 104 extending from the proximal end of first arm 102A to the proximal end of second arm 102B. The distal end of first arm 102A abuts the proximal end of a first fluke 106A. With reference to FIG. 8 it will be appreciated that first fluke 106A defines a first passageway 124A. in the exemplary embodiment of FIG. 8, first passageway 124A has a generally square cross-sectional shape. It will be appreciated, however, that first passageway 124A may have various cross-sectional shapes without deviating from the spirit and scope of the present detailed description.

A second fluke 106B extends distally from second arm 102B with the proximal end of second fluke 106B abutting the distal end of second arm 102B. With reference to FIG. 8, it will be appreciated that second fluke 106B has a lateral extent that is larger than a lateral extent of second arm 102B. Second fluke 106B is mounted eccentrically to second arm 102B in the embodiment of FIG. 8. Similarly, first fluke 106A is mounted eccentrically to first arm 102A and first fluke 106A has a lateral extent that is larger than a lateral extent of first arm 102A.

A proximal direction is illustrated with an arrow P in FIG. 8. A distal direction is illustrated with a second arrow D in FIG. 8. With reference to FIG. 8A, it will be appreciated that first fluke 106A of first arm 102A includes a first point 120A and a first barb 122A. Second fluke 106B includes a second point 120B and a second barb 122B. In FIG. 8, first point 120A and second point 120B are shown generally pointing in the distal direction indicated by arrow D. Also in FIG. 8, first barb 122A and second barb 122B are shown generally pointing in the proximal direction indicated by arrow P. With reference to FIG. 8, it will be appreciated that first fluke 106A includes a first proximal surface 108A projecting at an outward angle in a proximal direction away from the distal end of first arm 102A. Second fluke 106B includes a second proximal surface 108B projecting at an outward angle in a proximal direction away from the distal end of second arm 102B.

Figure 9:
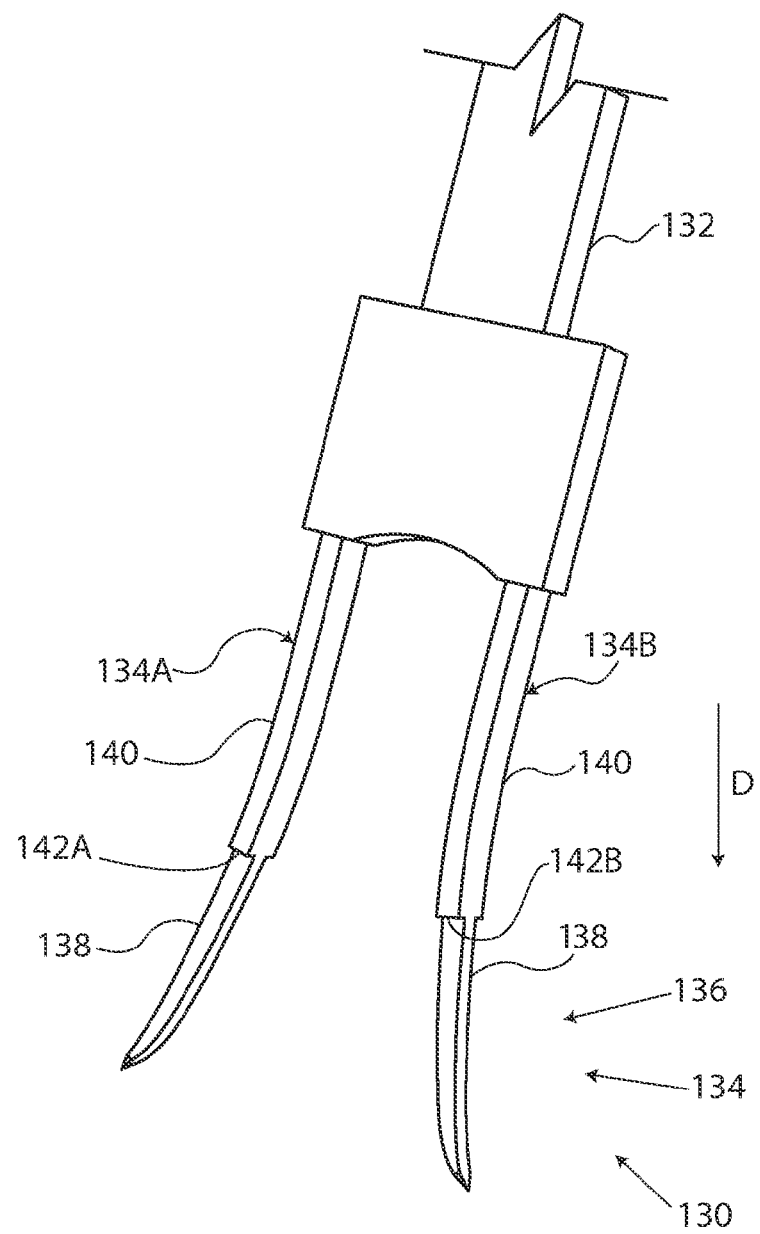
FIG. 9 is a perspective view showing a staple push rod that may be used in conjunction with the staple shown in the previous Figure.

FIG. 9 is a perspective view showing a staple push rod 130 that may be used in conjunction with staple 100 shown in the previous Figure. Staple push rod 130 includes a shaft 132 and a pair of stakes 134 extending distally beyond a distal end of shaft 132. The distal direction is indicated with an arrow D in FIG. 9. Stakes 134 include a first stake 134A and a second stake 134B. First stake 134A and second stake 134B form a fork 136.

In the embodiment of FIG. 9, each stake 134 has a distal portion 138 and a proximal portion 140. In some useful embodiments, each distal portion 138 is dimensioned to extend into a passage defined by a staple. In the embodiment of FIG. 9, each proximal portion 140 has a width larger than a width of each distal portion 138 so that a shoulder of each proximal portion 140 contacts a proximal surface of the staple to apply pushing forces thereto. First stake 134A comprises a first shoulder 142A and second stake 134B comprises a second shoulder 142B. Although depicted as a shoulder to provide pushing force to the staple, other designs can be utilized. For example, any larger cross section proximal portion can provide a pushing force, such as a conical increase in profile. In the embodiment of FIG. 9, proximal portion 140 of first stake 134A and the proximal portion 140 of second stake 134B diverge from one another as they extend in distal direction D away from shaft 132. In some applications, this arrangement may cause pushing forces applied to two flukes of a staple to have a laterally outward component.

In FIG. 9, first stake 134A and second stake 134B are shown assuming a substantially unstressed state. It will be appreciated that first stake 134A and second stake 134B can be resiliently urged to assume shapes other than the shape shown in FIG. 9. For example, first stake 134A and second stake 134B may be urged together so that fork 136 can be inserted into a lumen having a diameter smaller than the distance between the distal points of first stake 134A and second stake 134B shown in FIG. 9.

FIG. 10A and FIG. 10B illustrate multiple plan views of an exemplary fixation tool 144 in accordance with the present detailed description. Fixation tool 144 incorporates staple push rod 130 and is useful in delivering staple 100. FIG. 10A and FIG. 10B may be referred to collectively as FIG. 10. It is customary to refer to multi-view projections using terms such as front view, top view, and side view. In accordance with this convention, FIG. 10A may be referred to as a top view of fixation tool 144 and FIG. 10B may be referred to as a side view of fixation tool 144. The terms top view and side view are used herein as a convenient method for differentiating between the views shown in FIG. 10. It will be appreciated that the elements shown in FIG. 10 may assume various orientations without deviating from the spirit and scope of this detailed description. Accordingly, the terms top view and side view should not be interpreted to limit the scope of the invention recited in the attached claims.

In the embodiment of FIG. 10, fixation tool 144 comprises a fixation tool shaft 146 that is attached to a handle 148. Fixation tool shaft 146 comprises a wall 150 defining a lumen 152. With reference to FIG. 10, it will be appreciated that fixation tool shaft 146 includes a first prong 154A and a second prong 156B that extend distally beyond a distal end 158 of lumen 152.

In FIG. 10, a staple 100 can be seen residing in lumen 152 of fixation tool shaft 146. For purposes of illustration, a distal portion of fixation tool shaft 146 is enlarged in FIG. 10 to better show staple 100. Staple 100 comprises a first arm 102A, a second arm 102B, and a bridge 104 extending from the proximal end of first arm 102A to the proximal end of second arm 102B. The distal end of first arm 102A abuts the proximal end of a first fluke 106A. Similarly, the distal end of second arm 102E abuts the proximal end of a second fluke 106B. In FIG. 10, first fluke 106A and second fluke 106B are shown extending distally from first arm 102A and second arm 102B, respectively.

Staple push rod 130 includes a shaft 132 and a pair of stakes 134 extending distally beyond a distal end of shaft 132. The distal direction is indicated with an arrow D in FIG. 10. Stakes 134 include a first stake 134A and a second stake 134B. In FIG. 10, a distal portion of each stake 134 can be seen extending through a passageway defined by staple 100. In the embodiment of FIG. 10, a trigger 160 is pivotably coupled to handle 148 of fixation tool 144. Trigger 160 is operatively coupled to staple push rod 130. In operation, staple push rod 130 will be advanced and/or retracted in an axial direction when trigger 160 is pivoted relative to handle 148.

Figure 11A:
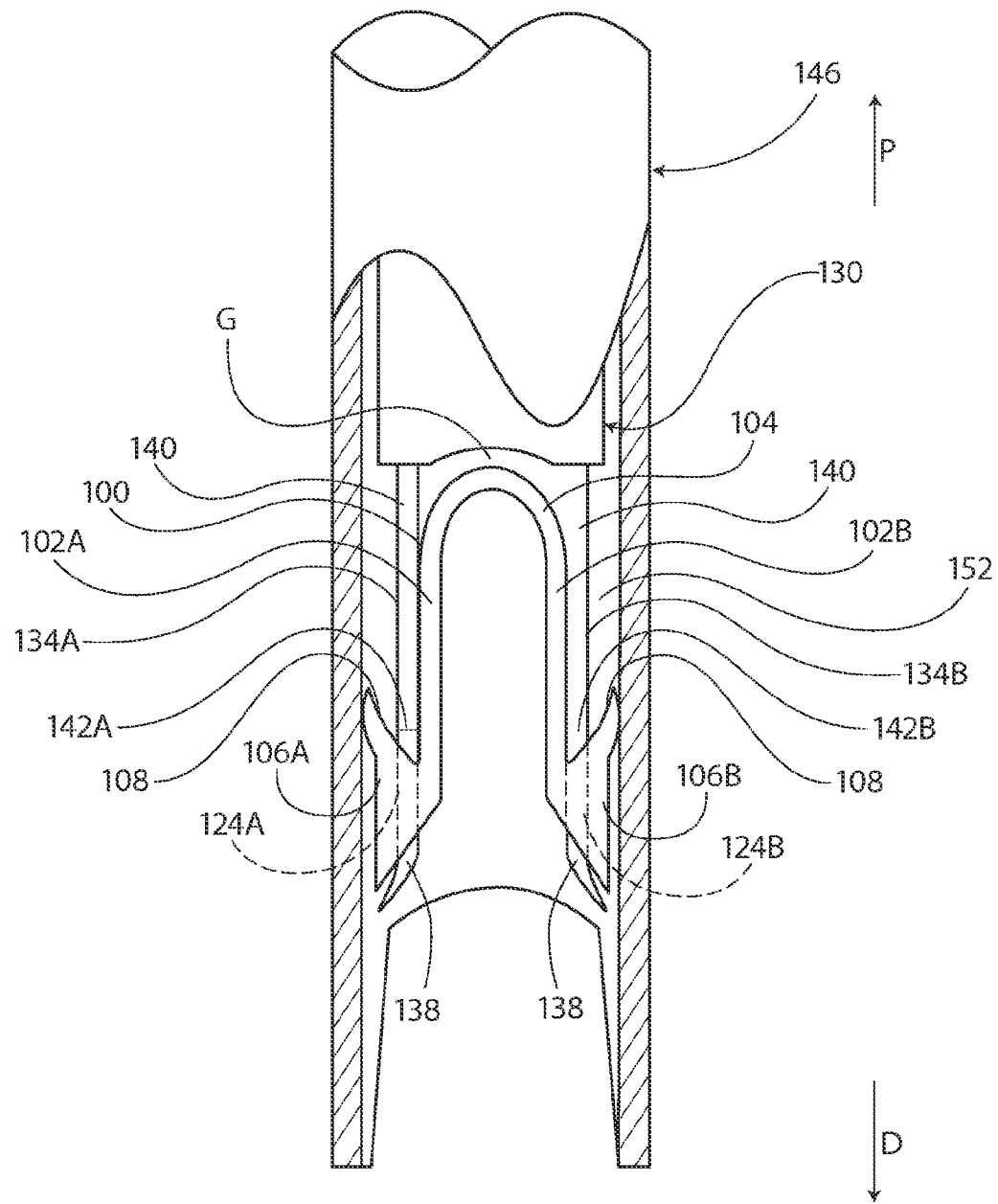
FIG. 11A is a further enlarged partial cross-sectional view of a distal portion of the fixation tool shaft shown in the previous Figure.

FIG. 11A is a further enlarged top view of a distal portion of fixation tool shaft 146 shown in the previous Figure. For purposes of illustration, fixation tool shaft 146 is shown in partial cross-section in FIG. 11A so that staple 100 is visible residing in lumen 152. With reference to FIG. 11A, it will be appreciated that staple 100 is disposed on a distal portion of staple push rod 130. Staple 100 comprises a first arm 102A, a second arm 102B, and a bridge 104 extending from the proximal end of first arm 102A to the proximal end of second arm 102B. The distal end of first arm 102A abuts the proximal end of a first fluke 106A. Similarly, the distal end of second arm 102B abuts the proximal end of a second fluke 106B. In FIG. 11, first fluke 106A and second fluke 106B are shown extending distally from first arm 102A and second arm 102B, respectively.

First fluke 106A of staple 100 defines a first passageway 124A. In FIG. 11A, a distal portion 138 of first stake 134A of staple push rod 130 can be seen extending through first passageway 124A defined by first fluke 106A. A distal portion 138 of second stake 134B of staple push rod 130 can be seen extending through a second passageway 124B defined by second fluke 106B of staple 100.

In FIG. 11A, a first shoulder 142A of first stake 134A is shown contacting proximal surface 108 of first fluke. Distal portion 138 of first stake 134A extends distally of first shoulder 142A and proximal portion 140 of first stake 134A extends proximally of first shoulder 142A. In some useful embodiments, the proximal portion of first stake 134A has a first thickness and the distal portion of first stake 134A has a second thickness different from the first thickness. In some particularly useful embodiments, the second thickness is less than the first thickness. In some applications, this may increase the flexibility of the distal portion of first stake 134A so that it bends more easily, and so that it withdraws from the staple with minimal force.

A second shoulder 142B of second stake 134B is shown contacting proximal surface 108 of second fluke 106 in FIG. 11A. A distal portion 138 of second stake 134B extends distally of second shoulder 142B and a proximal portion 140 of second stake 134B extends proximally of second shoulder 142B. In some useful embodiments, the proximal portion of second stake 134B has a first thickness and the distal portion of second stake 134B has a second thickness different from the first thickness. In some particularly useful embodiments, the second thickness is less than the first thickness. In some applications, this may increase the flexibility of the distal portion of first stake 134A so that it bends more easily, and so that it withdraws from the staple with minimal force.

With reference to FIG. 11A, it will be appreciated that there is a gap G between staple push rod 130 and bridge 104 of staple 100. In some applications, gap G allows staple 100 to be placed in tension without bridge 104 contacting staple push rod 130. Staple 100 may be placed in tension, for example, as staple 100 is advanced into a target tissue.

Figure 11B:
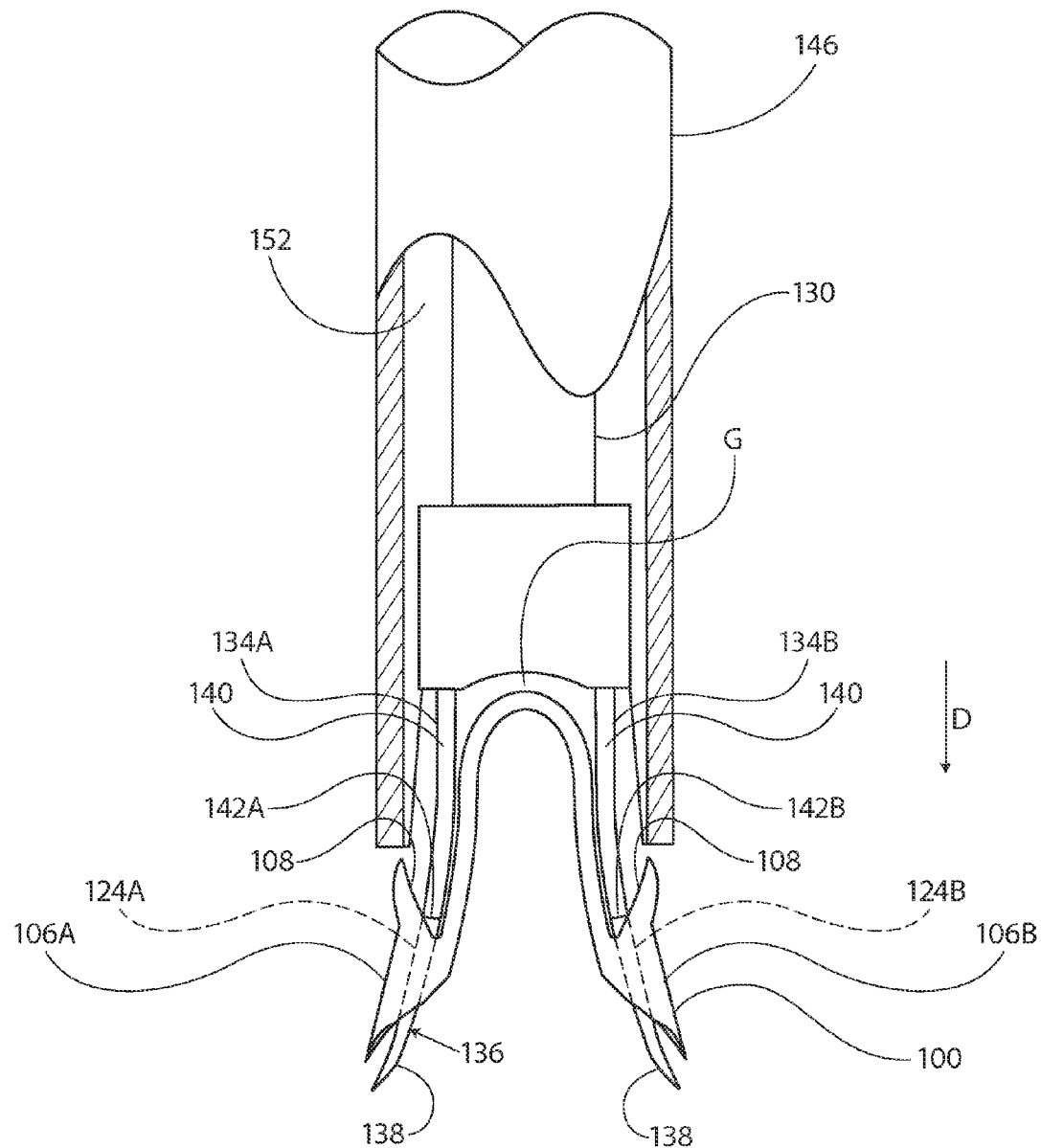
FIG. 11B is an additional partial cross-sectional view showing a staple carried by a staple push rod and a fixation tool shaft disposed about the staple push rod.

FIG. 11B is an additional top view showing a distal portion of fixation tool shaft 146, staple push rod 130, and staple 100. By comparing FIG. 11A and FIG. 11B, it will be appreciated that staple push rod 130 and staple 100 have been advanced in a distal direction D relative to fixation tool shaft 146. In FIG. 11B, staple 100 is shown extending out of lumen 152 defined by fixation tool shaft 146.

In FIG. 11B, a distal portion 138 of first stake 134A of staple push rod 130 can be seen extending through a first passageway 124A defined by first fluke 106A of staple 100. In FIG. 11B, a first shoulder 142A of first stake 134A is shown contacting proximal surface 108 of first fluke 106A. Distal portion 138 of first stake 134A extends distally of first shoulder 142A and proximal portion 140 of first stake 134A extends proximally of first shoulder 142A. In some useful embodiments, the proximal portion of first stake 134A has a first width and the distal portion of first stake 134A has a second width different from the first width. In some particularly useful embodiments, the first width is greater than the first width. The arrangement allows the proximal portion of stake to engage a proximal surface of the staple to apply pushing forces to the staple.

In FIG. 11B, a distal portion 138 of second stake 134B of staple push rod 130 can be seen extending through a second passageway 124B defined by second fluke 106B of staple 100. In FIG. 11B, a second shoulder 142B of second stake 134B is shown contacting proximal surface 108 of second fluke 106B. In the embodiment of FIG. 11B, proximal portion 140 of second stake 134B may apply pushing force to proximal surface 108 of second stake 134B. Proximal portion 140 of second stake 134B extends proximally of second shoulder 142B and distal portion 138 of second stake 134B extends distally of second shoulder 142B. In the embodiment of FIG. 11B, proximal portion 140 of second stake 134B has a width larger than the width of distal portion 138 of second stake 134B so that the shoulder 142 of second stake 134B contacts proximal surface 108 of second fluke 106B to apply pushing forces thereto.

In the embodiment of FIG. 11B, first stake 134A and second stake 134B are in a substantially unstressed state. It will be appreciated that first stake 134A and second stake 13413 can be resiliently urged to assume shapes other than the shape shown in FIG. 11. For example, first stake 134A and second stake 134B may be urged together so that fork 136 of staple push rod 130 and staple 100 can be inserted into lumen 152 defined by fixation tool shaft 146.

With reference to FIG. 11B, it will be appreciated that there is a gap G between staple push rod 130 and bridge 104 of staple 100. In some applications, gap G allows staple 100 to be placed in tension without bridge 104 contacting staple push rod 130. In some applications, placing staple 100 under tension may urge first fluke 106 and second fluke 106 into orientations which lock staple 100 into a target tissue. For example, first fluke 106A and second fluke 106B may be rotated so that a barb of each fluke engages the target tissue. When this is the case, the tension on the staple may keep first fluke 106A and second fluke 106B in the rotated position. Also when this is the case, the barbs of the rotated flukes may inhibit staple pullout.

Figure 12C:
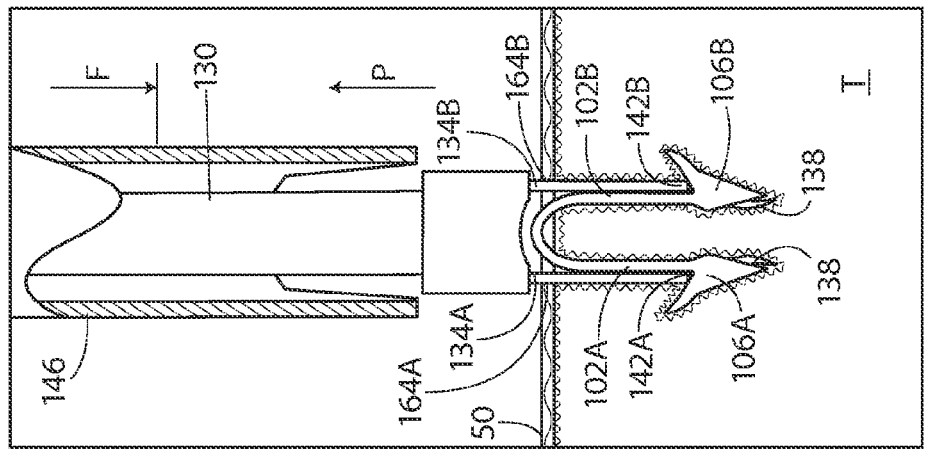
FIG. 12A through FIG. 12C are a sequence of plan views illustrating an exemplary method and apparatus in accordance with the present detailed description.
Figure 12B:
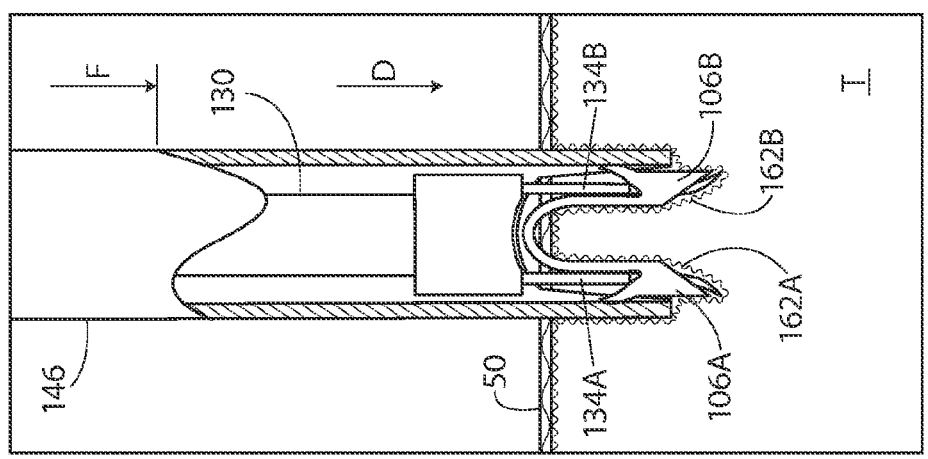
Figure 12A:
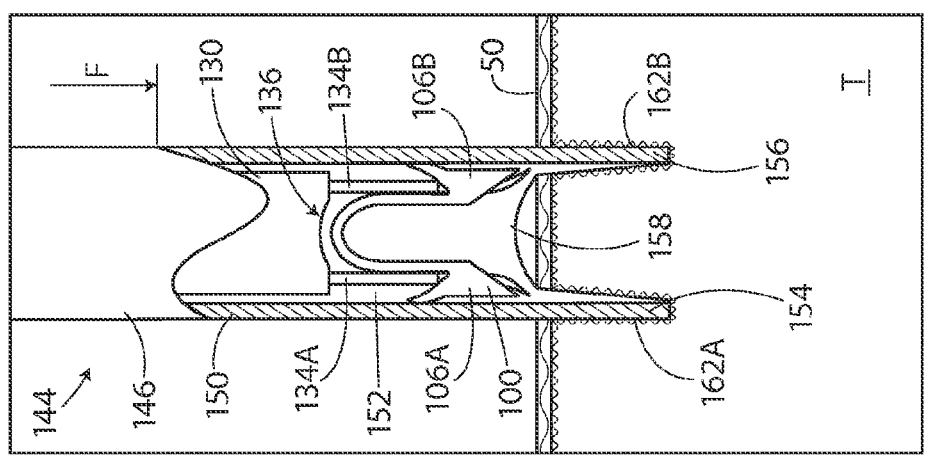

FIG. 12A through FIG. 12C are a sequence of plan views illustrating an exemplary method in accordance with the present detailed description. FIG. 12A, FIG. 12B, and FIG. 12C may be collectively referred to as FIG. 12. The exemplary method illustrated in FIG. 12 may be used, for example, to fix a tendon repair implant 50 to a target tissue T using a staple 100.

At FIG. 12A, a fixation tool 144 has been used to form a first pilot hole 162A and a second pilot hole 162B in target tissue T. In the embodiment of FIG. 12, fixation tool 144 includes a fixation tool shaft 146 comprising a wall 150 defining a lumen 152. With reference to FIG. 12, it will be appreciated that fixation tool shaft 146 includes a first prong 154A and a second prong 156B that extend distally beyond a distal end 158 of lumen 152. In the embodiment of FIG. 12A, first prong 154A and second prong 156B have been urged into tissue T to form first pilot hole 162A and second pilot hole 162B. In FIG. 12A a distally directed force F applied to fixation tool shaft 146 is illustrated using an arrow. Force F may be produced, for example, by pushing on a handle that is fixed to a proximal portion of fixation tool shaft 146. It will be appreciated that in some embodiments, such as the embodiment depicted in FIG. 6, one of the first and second pilot holes may be formed through the sheet-like implant and the target tissue, and the other pilot hole may be formed directly in the target tissue without passing through the sheet-like implant. In other words, in various embodiments staples may straddle the perimeter edge of the sheet-like implant (as shown in FIG. 6), may be applied adjacent to the perimeter, and/or be applied to a central region of the implant. In some embodiments, the staples may be used to attach the implant to soft tissue and/or to bone. In FIG. 12A, a staple 100 can be seen residing in lumen 152 of fixation tool shaft 146. For purposes of illustration, fixation tool shaft 146 is shown in partial cross-section in FIG. 12A so that staple 100 is visible residing in lumen 152. With reference to FIG. 12, it will be appreciated that staple 100 is carried by a fork 136 comprising a first stake 134A and a second stake 134B. In FIG. 12A, a distal portion of first stake 134A of staple push rod 130 can be seen extending through a first passageway defined by first fluke 106A. A distal portion of second stake 134B of staple push rod 130 can be seen extending through a second passageway defined by second fluke 106B of staple 100.

In some useful embodiments, each stake is positioned relative to a prong along an inner surface of fixation tool shaft 146 so that the stakes advance into the pilot holes when the stakes are moved in a distal direction. Staple push rod 130 is slidably disposed within lumen 152 defined by along fixation tool shaft 146. Fixation tool 144 includes a mechanism that is capable of creating relative axial motion between staple push rod 130 and fixation tool shaft 146 so that staple push rod 130 slides along fixation tool shaft 146.

At FIG. 12B, relative motion has been created between staple push rod 130 and fixation tool shaft 146 while distally directed force F has been continuously applied to fixation tool shaft 146. By comparing FIG. 12B and FIG. 12A, it will be appreciated that first stake 134A and second stake 134B have been advanced in a distal direction D. With reference to FIG. 12, it will also be appreciated that first stake 134A and second stake 134B have advanced into first pilot hole 162A and second pilot hole 162B, respectively. In FIG. 12B, first fluke 106A is shown residing in first pilot hole 162. Second fluke 106B is residing in second pilot hole 162 in the embodiment of FIG. 12B.

At FIG. 12C, additional relative motion has been created between staple push rod 130 and fixation tool shaft 146 while distally directed force F has been continuously applied to fixation tool shaft 146. By comparing FIG. 12C and FIG. 12B, it will be appreciated that the relative motion between staple push rod 130 and fixation tool shaft 146 has moved fixation tool shaft 146 in a proximal direction P.

By comparing FIG. 12C and FIG. 12B, it will also be appreciated that first arm 102A of staple 100 has been bent and first fluke 106A has been rotated to a toggled position. In the exemplary embodiment of FIG. 12C, force applied to first fluke 106A by first shoulder 142A has caused first fluke 106A to rotate. Also in the embodiment of FIG. 12C, the rotation of first fluke 106A has caused some bending in the distal portion 138 of first stake 134A. With continuing reference to FIG. 12C and FIG. 12B, it will be appreciated that second arm 102B of staple 100 has been bent and second fluke 106A has been rotated to a toggled position. In the exemplary embodiment of FIG. 12C, force applied to second fluke 106*b* by second shoulder 142B has caused second fluke 106B to rotate. Also in the embodiment of FIG. 12C, the rotation of second fluke 106B has caused some bending in the distal portion 138 of second stake 134B.

With reference to FIG. 12C, it will be appreciated that a first through hole 164A and a second through hole 164B have been formed in tendon repair implant 50. In the embodiment of FIG. 12, first through hole 164A and a second through hole 164B were created by urging first prong 154A and second prong 156B of fixation tool shaft 146 through tendon repair implant 50.

FIG. 13A, FIG. 13B, and FIG. 13C are multiview projections illustrating a fixation tool shaft 146 shown in the previous Figures. FIG. 13D is a cross-sectional view of fixation tool shaft 146 sectioned along cutting plane D-D illustrated in FIG. 13C. These Figures may be collectively referred to as FIG. 13. Fixation tool shaft 146 of FIG. 13 comprises a wall 150 defining a lumen 152. A first prong 154A and a second prong 156B of fixation tool shaft 146 extend distally beyond a distal end 158 of lumen 152.

With reference to FIG. 13, it will be appreciated that fixation tool shaft 146 comprises a proximal portion 170, a distal portion 168 and an intermediate portion 166 disposed between proximal portion 170 and distal portion 168. In the embodiment of FIG. 13, distal portion 168 has an axial extent DA, a major lateral extent LA and a minor lateral extent LB. With reference to FIG. 13, it will be appreciated that axial extent DA is greater than both minor lateral extent LB and major lateral extent LA.

Figure 14:
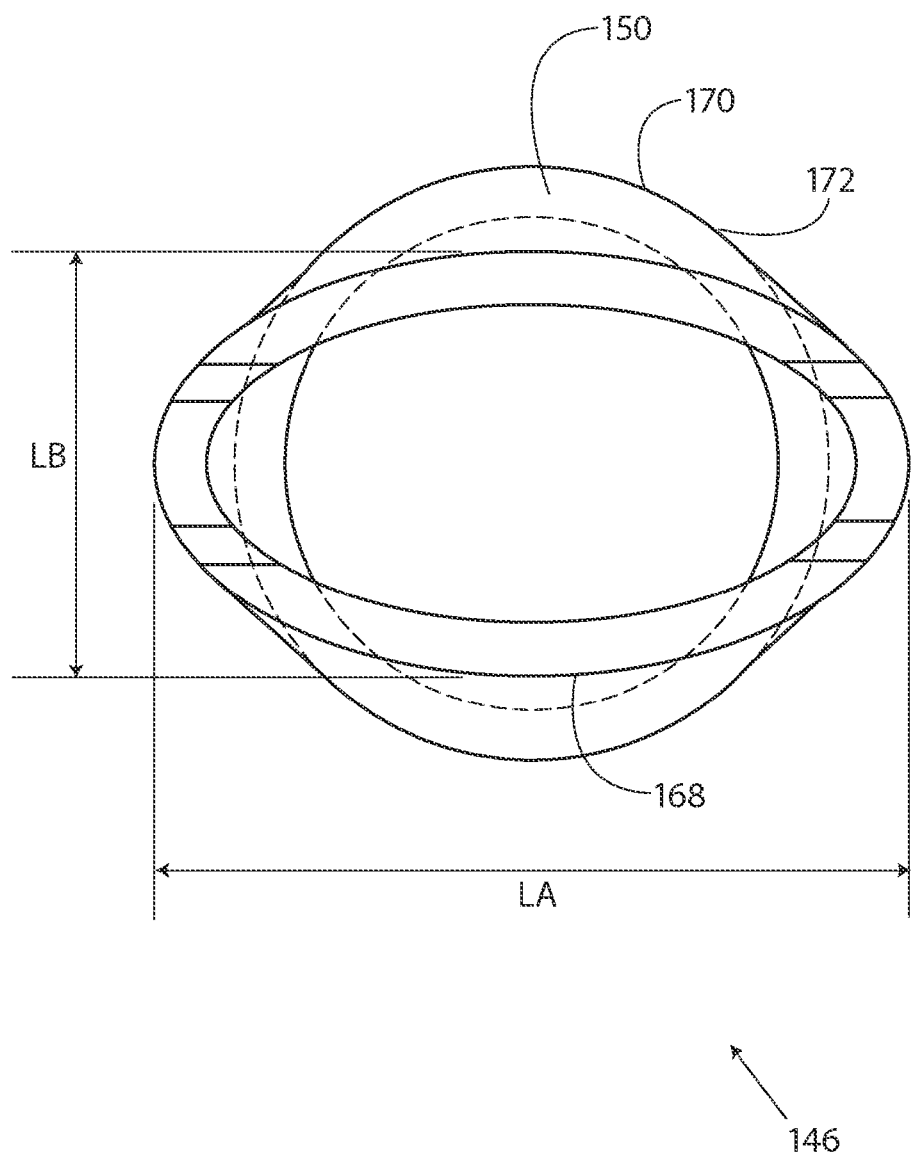
FIG. 14 is an enlarged axial view of the fixation tool shaft shown in the previous Figure.

FIG. 14 is an enlarged axial view of fixation tool shaft 146 shown in the previous Figure. With reference to FIG. 14, it will be appreciated that proximal portion 170 of fixation tool shaft 146 comprises a wall 150 having an outer surface 172. In FIG. 14, outer surface 172 is illustrated using a circle. Thus, it will be appreciated that proximal portion 170 of fixation tool shaft 146 has a generally cylindrical outer shape in the exemplary embodiment of FIG. 14. In the exemplary embodiment of FIG. 14, fixation tool shaft 146 has a generally uniform wall thickness. Accordingly, the shape of proximal portion 170 may be generally described as a cylindrical tube. The shape of distal portion 168 may be described as a cylindrical-tube that has been partially flattened. In the exemplary embodiment of FIG. 14, distal portion 168 of fixation tool shaft 146 has a major lateral extent LA and a minor lateral extent LB. With reference to FIG. 14, it will be appreciated that major lateral extent LA is greater than minor lateral extent LB.

Figure 15:
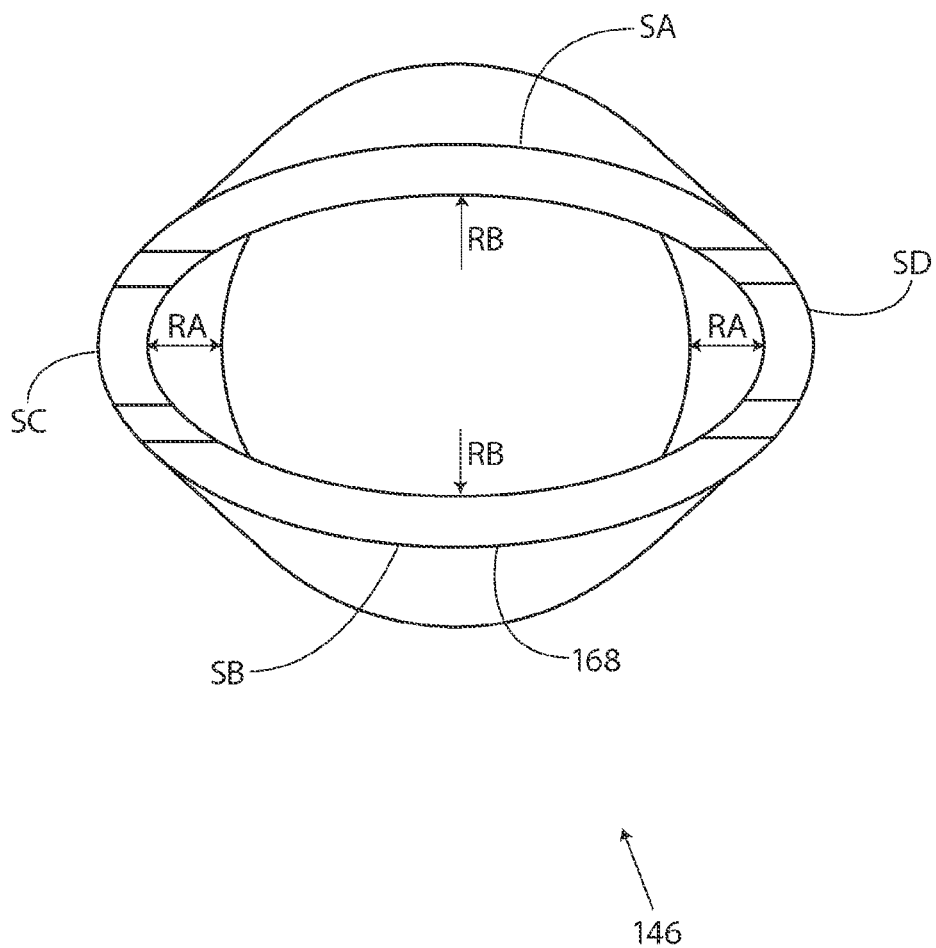
FIG. 15 is an additional enlarged axial view of the fixation tool shaft shown in the previous Figure.

FIG. 15 is an additional enlarged axial view of fixation tool shaft 146. With reference to FIG. 15, it will be appreciated that distal portion 168 of fixation tool shaft 146 comprises a first major side SA, a second major side SB, a first minor side SC, and a second minor side SD. In the exemplary embodiment of FIG. 15, each minor side has a first central radius RA and each major side has a second central radius RB. With reference to FIG. 15, it will be appreciated that second central radius RB is greater than first central radius RA. In the exemplary embodiment of FIG. 15, first major side SA, second major side SB, first minor side SC, and second minor side SD each have a generally convex shape. In the exemplary embodiment of FIG. 15, each minor side is generally more convex than each major side.

Figure 16:
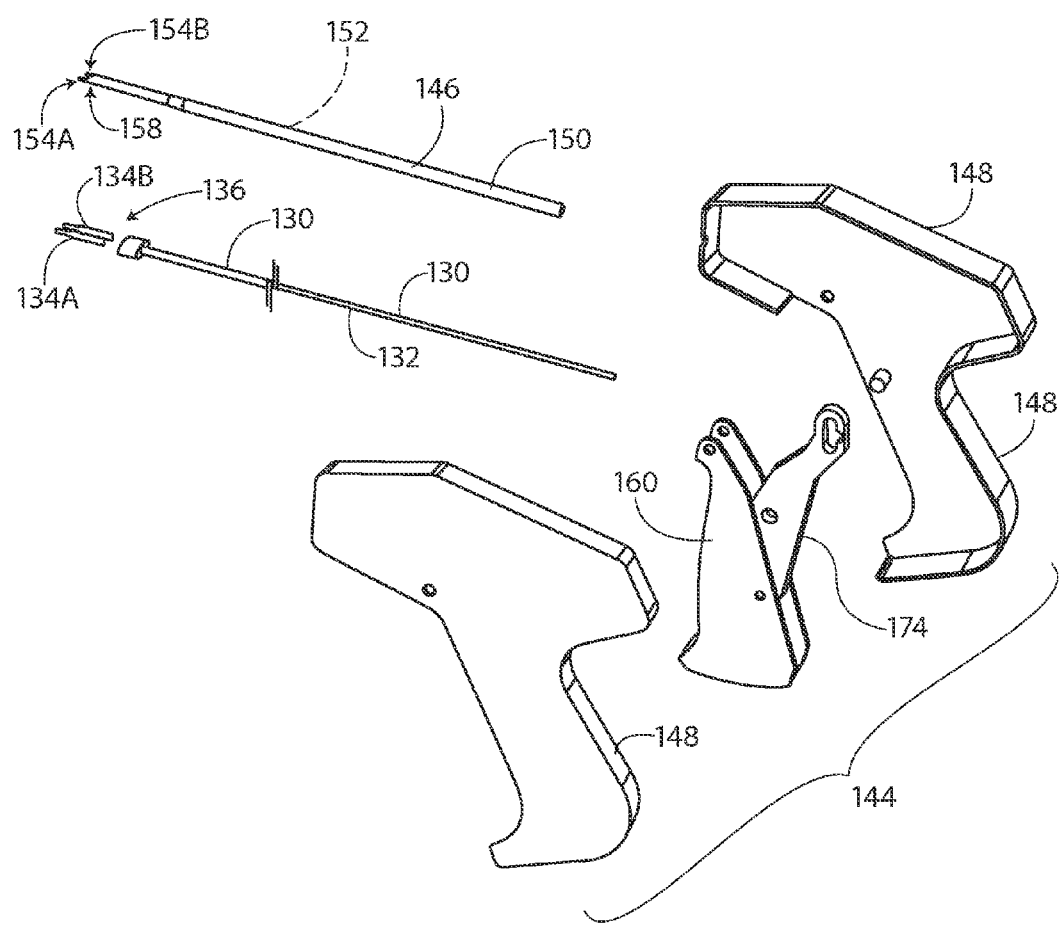
FIG. 16 is an exploded isometric view of an exemplary fixation tool in accordance with this detailed description.

FIG. 16 is an exploded isometric view of an exemplary fixation tool 144 in accordance with this detailed description. In the embodiment of FIG. 16, fixation tool 144 comprises a fixation tool shaft 146 and a handle 148. In FIG. 16, handle 148 is exploded into two pieces. A proximal portion of fixation tool shaft 146 is fixed to handle 148 when fixation tool 144 is in an assembled state. Fixation tool shaft 146 comprises a wall 150 defining a lumen 152. With reference to FIG. 16, it will be appreciated that fixation tool shaft 146 includes a first prong 154A and a second prong 156B that extend distally beyond a distal end 158 of lumen 152.

When fixation tool 144 is in an assembled state a staple push rod 130 extends into lumen 152 of fixation tool shaft 146. Staple push rod 130 comprises a fork 136 and a shaft 132. Fork 136 comprises a first stake 134A and a second stake 1348. Shaft 132 is coupled between fork 136 and a lever 174. Lever 174 is coupled to a trigger 160. Trigger 160 is pivotably coupled to handle 148 of fixation tool 144 when fixation tool 144 is in an assembled state. In operation, staple push rod 130 will be advanced and/or retracted in an axial direction when trigger 160 is pivoted relative to handle 148.

While exemplary embodiments of the present invention have been shown and described, modifications may be made, and it is therefore intended in the appended claims and subsequently filed claims to cover all such changes and modifications which fall within the true spirit and scope of the invention.

The invention claimed is:

1. A staple for attaching a sheet-like implant to tissue or bone comprising:
a first arm, having a proximal end and a distal end, and a second arm having a proximal end and a distal end with a bridge extending from the proximal end of the first arm to the proximal end of the second arm;
a first fluke having a proximal end abutting the distal end of the first arm, the first fluke extending distally from the first arm, the first fluke having a lateral extent larger than a lateral extent of the first arm and mounted eccentrically thereto, the first fluke including a proximal surface projecting at an outward angle in a proximal direction away from the distal end of the first arm to engage the tissue or bone when inserted therein, the first fluke including a distal pointed surface, wherein there are no barbs or projections extending from the first arm towards the second arm, thereby causing the first fluke to rotate in response to a pullout force on the bridge; and,
a second fluke having a proximal end abutting the distal end of the second arm and extending distally, the second fluke having a lateral extent larger than the lateral extent of the second arm and mounted eccentrically thereto with the second fluke including a proximal surface projecting at an outward angle in a proximal direction and away from the second arm near the proximal end of the second fluke to engage the tissue or bone when inserted therein, the second fluke including a distal pointed surface, wherein there are no bards or projections extending from the second arm toward the first arm, thereby causing the second fluke to rotate in response to a pullout force on the bridge,
wherein each of the first fluke and the second fluke include a lumen extending from the proximal end to the distal end therefor spaced laterally from the respective arm mounted thereto; and
wherein each lumen of the first and the second fluke is sized to receive a first stake and a second stake, respectively, of a staple delivery device therethrough.

2. The staple of claim 1, wherein the lateral extent of each of the flukes is at least about three times the lateral extent of the arm adjacent thereto.

3. The staple of claim 2, wherein the lateral extent of the first arm and the second arm is about 0.3 mm to about 3.0 mm.

4. The staple of claim 2, wherein the first arm, second arm, first fluke, second fluke, proximal surfaces and bridge are integrally formed of a polymeric material.

5. The staple of claim 4, wherein the polymeric material is bioresorbable.

6. The staple of claim 1, wherein the proximal surface of the first fluke engages the first stake and the proximal surface of the second fluke engages the second stake to receive pushing forces for inserting the staple into the tissue.

7. The staple of claim 1, wherein at least a portion of each of the lengths of the first and the second arms is flexible to allow flexing of the first and second flukes relative thereto to achieve rotational engagement of each fluke to the tissue or bone.

8. The staple of claim 1, wherein the proximal surface projecting at an outward angle of the first fluke includes a notch that divides a portion of the proximal surface projecting at an outward angle of the first fluke into a first barb and a second barb.

9. The staple of claim 8, wherein the proximal surface projecting at an outward angle of the second fluke includes a notch that divides a portion of the proximal surface projecting at an outward angle of the second fluke into a first barb and a second barb.

10. The staple of claim 9, wherein when viewed along a longitudinal axis of the second arm the notch of the second fluke bifurcates the portion of the proximal surface projecting at an outward angle of the second fluke to form the first barb and second barb of the second fluke.

11. The staple of claim 8, wherein when viewed along a longitudinal axis of the first arm the notch of the first fluke bifurcates the portion of the proximal surface projecting at an outward angle of the first fluke to form the first barb and second barb of the first fluke.

12. The staple of claim 1, the distal pointed surface of the first fluke including a distal surface projecting at an outward angle in a distal direction away from the distal end of the first arm to engage the tissue or bone when inserted therein, the distal pointed surface of the second fluke including a distal surface projecting at an outward angle in a distal direction away from the distal end of the second arm to engage the tissue or bone when inserted therein.

13. The staple of claim 1, wherein the distal pointed surface of the first fluke is asymmetrical relative to a longitudinal axis of the first fluke.

14. The staple of claim 1, wherein the distal pointed surface of the second fluke is asymmetrical relative to a longitudinal axis of the second fluke.

15. A staple for attaching a sheet-like implant to tissue or bone comprising:
a first arm, having a proximal end and a distal end, and a second arm having a proximal end and a distal end with a bridge extending from the proximal end of the first arm to the proximal end of the second arm;
a first fluke having a proximal end abutting the distal end of the first arm, the first fluke extending distally from the first arm, the first fluke having a lateral extent larger than a lateral extent of the first arm and mounted eccentrically thereto, the first fluke including a proximal surface projecting at an outward angle in a proximal direction away from the distal end of the first arm to engage the tissue or bone when inserted therein, the first fluke including a distal pointed surface, wherein there are no barbs or projections extending from the first arm towards the second arm, thereby causing the first fluke to rotate in response to a pullout force on the bridge; and,
a second fluke having a proximal end abutting the distal end of the second arm and extending distally, the second fluke having a lateral extent larger than the lateral extent of the second arm and mounted eccentrically thereto with the second fluke including a proximal surface projecting at an outward angle in a proximal direction and away from the second arm near the proximal end of the second fluke to engage the tissue or bone when inserted therein, the second fluke including a distal pointed surface, wherein there are no barbs or projections extending from the second arm toward the first arm, thereby causing the second fluke to rotate in response to a pullout force on the bridge,
wherein each of the first fluke and the second fluke include a lumen extending from the proximal end to the distal end therefor spaced laterally from the respective arm mounted thereto; and
wherein the proximal surface projecting at an outward angle of the first fluke includes a notch that divides a portion of the proximal surface projecting at an outward angle of the first fluke into a first barb and a second barb.

16. The staple of claim 15, wherein when viewed along a longitudinal axis of the first arm the notch of the first fluke bifurcates the portion of the proximal surface projecting at an outward angle of the first fluke to form the first barb and second barb of the first fluke.

17. The staple of claim 15, wherein the proximal surface projecting at an outward angle of the second fluke includes a notch that divides a portion of the proximal surface projecting at an outward angle of the second fluke into a first barb and a second barb.

18. The staple of claim 17, wherein when viewed along a longitudinal axis of the second arm the notch of the second fluke bifurcates the portion of the proximal surface projecting at an outward angle of the second fluke to form the first barb and second barb of the second fluke.

19. The staple of claim 15, wherein at least a portion of each of the lengths of the first and the second arms is flexible to allow flexing of the first and second flukes relative thereto to achieve rotational engagement of each fluke to the tissue or bone.

20. The staple of claim 15, the distal pointed surface of the first fluke including a distal surface projecting at an outward angle in a distal direction away from the distal end of the first arm to engage the tissue or bone when inserted therein, the distal pointed surface of the second fluke including a distal surface projecting at an outward angle in a distal direction away from the distal end of the second arm to engage the tissue or bone when inserted therein.

* * * * *